United States Patent [19]

Schnur et al.

[11] Patent Number: 5,747,498
[45] Date of Patent: May 5, 1998

[54] ALKYNYL AND AZIDO-SUBSTITUTED 4-ANILINOQUINAZOLINES

[75] Inventors: Rodney Caughren Schnur, Noank, Conn.; Lee Daniel Arnold, Westborough, Mass.

[73] Assignee: Pfizer Inc., New York, N.Y.

[21] Appl. No.: 653,786

[22] Filed: May 28, 1996

Related U.S. Application Data

[63] Continuation-in-part of PCT/IB95/00436, Jun. 6, 1995.

[51] Int. Cl.⁶ .............. A61K 31/495; A61K 31/505; C07D 239/70; C07D 239/94
[52] U.S. Cl. .............. 514/259; 544/283; 544/293
[58] Field of Search ................ 544/283, 293; 514/259

[56] References Cited

U.S. PATENT DOCUMENTS

| | | | |
|---|---|---|---|
| 5,256,781 | 10/1993 | Primeau | 514/259 |
| 5,457,105 | 10/1995 | Barker | 514/259 |
| 5,475,001 | 12/1995 | Barker | 514/259 |

FOREIGN PATENT DOCUMENTS

| | | |
|---|---|---|
| 520722 | 12/1992 | European Pat. Off. . |
| 566226 | 10/1993 | European Pat. Off. . |
| 602851 | 6/1994 | European Pat. Off. . |
| 635498 | 1/1995 | European Pat. Off. . |
| WO92/20642 | 11/1992 | WIPO . |
| WO95/15758 | 6/1995 | WIPO . |

*Primary Examiner*—Matthew V. Grumbling
*Attorney, Agent, or Firm*—Peter C. Richardson; Paul H. Ginsburg; Bryan C. Zielinski

[57] ABSTRACT

The invention relates to compounds of the formula

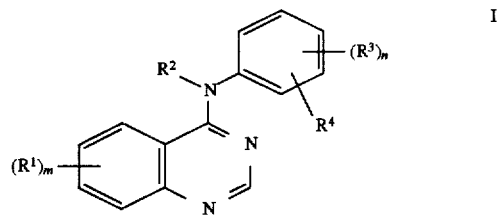

and to pharmaceutically acceptable salts thereof, wherein $R^1$, $R^2$, $R^3$, $R^4$, n and m are as defined herein. The compounds of formula I are useful in the treatment of hyperproliferative diseases, such as cancer. The invention further relates to processes of making the compounds of formula I and to methods of using such compounds in the treatment of hyperproliferative diseases.

32 Claims, No Drawings

ALKYNYL AND AZIDO-SUBSTITUTED 4-ANILINOQUINAZOLINES

This application is a continuation-in-part of PCT international application number PCT/IB95/00436, filed Jun. 6, 1995, which designates the United States.

BACKGROUND OF THE INVENTION

This invention relates to 4-(substituted phenylamino) quinazoline derivatives which are useful in the treatment of hyperproliferative diseases, such as cancers, in mammals.

Many of the current treatment regimes for cancer utilize compounds which inhibit DNA synthesis. Such compounds are toxic to cells generally but their toxic effect on the rapidly dividing tumor cells can be beneficial. Alternative approaches to anti-cancer agents which act by mechanisms other than the inhibition of DNA synthesis have been explored in order to enhance the selectivity of action against cancer cells.

It is known that a cell may become cancerous by virtue of the transformation of a portion of its DNA into an oncogene (i.e. a gene which, on activation, leads to the formation of malignant tumor cells). Many oncogenes encode proteins which are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are large enzymes which span the cell membrane and possess an extracellular binding domain for growth factors such as epidermal growth factor, a transmembrane domain, and an intracellular portion which functions as a kinase to phosphorylate specific tyrosine residues in proteins and hence to influence cell proliferation. It is known that such kinases are frequently aberrantly expressed in common human cancers such as breast cancer, gastrointestinal cancer such as colon, rectal or stomach cancer, leukemia, and ovarian, bronchial or pancreatic cancer. It has also been shown that epidermal growth factor receptor (EGFR) which possesses tyrosine kinase activity is mutated and/or overexpressed in many human cancers such as brain, lung, squamous cell, bladder, gastric, breast, head and neck, oesophageal, gynecological and thyroid tumors.

Accordingly, it has been recognized that inhibitors of receptor tyrosine kinases are useful as a selective inhibitors of the growth of mammalian cancer cells. For example, erbstatin, a tyrosine kinase inhibitor selectively attenuates the growth in athymic nude mice of a transplanted human mammary carcinoma which expresses epidermal growth factor receptor tyrosine kinase (EGFR) but is without effect on the growth of another carcinoma which does not express the EGF receptor.

Various other compounds, such as styrene derivatives, have also been shown to possess tyrosine kinase inhibitory properties. More recently five European patent publications, namely EP 0 566 226 A1, EP 0 602 851 A1, EP 0 635 507 A1, EP 0 635 498 A1 and EP 0 520 722 A1 have disclosed that certain quinazoline derivatives possess anti-cancer properties which result from their tyrosine kinase inhibitory properties. Also PCT publication WO 92/20642 discloses bis-mono and bicyclic aryl and heteroaryl compounds as tyrosine kinase inhibitors.

Although the anti-cancer compounds described above make a significant contribution to the art there is a continuing search in this field of art for improved anti-cancer pharmaceuticals.

SUMMARY OF THE INVENTION

This invention relates to compounds of the formula

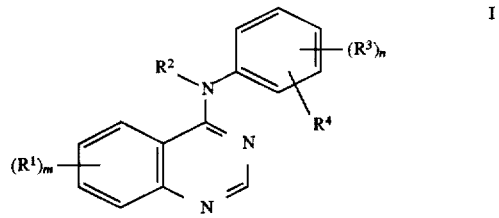

and to pharmaceutically acceptable salts and prodrugs thereof, wherein:

m is 1, 2, or 3;

each $R^1$ is independently selected from the group consisting of hydrogen, halo, hydroxy, hydroxyamino, carboxy, nitro, guanidino, ureido, cyano, trifluoromethyl, and -($C_1$–$C_4$ alkylene)-W-(phenyl) wherein W is a single bond, O, S or NH;

or each $R^1$ is independently selected from $R^9$ and ($C_1$–$C_4$) -alkyl substituted by cyano, wherein $R^9$ is selected from the group consisting of $R^5$, —$OR^6$, —$NR^6R^6$, —$C(O)R^7$, —$NHOR^5$, —$OC(O)R^6$, cyano, A and —$YR^5$; $R^5$ is $C_1$–$C_4$ alkyl; $R^6$ is independently hydrogen or $R^5$; $R^7$ is $R^5$, —$OR^6$ or —$NR^6R^6$; A is selected from piperidino, morpholino, pyrrolidino, 4-$R^6$-piperazin-1-yl, imidazol-1-yl, 4-pyridon-1-yl, -($C_1$–$C_4$ alkylene)($CO_2H$), phenoxy, phenyl, phenylsulfanyl, $C_2$–$C_4$ alkenyl, and -($C_1$–$C_4$ alkylene)$C(O)NR^6R^6$; and Y is S, SO, or $SO_2$; wherein the alkyl moieties in $R^5$, —$OR^6$ and —$NR^6R^6$ are optionally substituted by one to three substituents independently selected from halo and $R^9$, and wherein the alkyl moieties of said optional substituents are optionally substituted by halo or $R^9$, with the proviso that two heteroatoms are not attached to the same carbon atom, and with the further proviso that no more than three $R^9$ groups may comprise a single $R^1$ group;

or each $R^1$ is independently selected from —$NHSO_2R^5$, phthalimido-($C_1$–$C_4$)-alkylsulfonylamino, benzamido, benzenesulfonylamino, 3-phenylureido, 2-oxopyrrolidin-1-yl, 2,5-dioxopyrrolidin-1-yl, and $R^{10}$-($C_2$–$C_4$)-alkanoylamino wherein $R^{10}$ is selected from halo, —$OR^6$, $C_2$–$C_4$ alkanoyloxy, —$C(O)R^7$, and —$NR^6R^6$; and wherein the foregoing $R^1$ groups are optionally substituted by 1 or 2 substituents independently selected from halo, $C_1$–$C_4$ alkyl, cyano, methanesulfonyl and $C_1$–$C_4$ alkoxy;

or two $R^1$ groups are taken together with the carbons to which they are attached to form a 5–8 membered ring that includes 1 or 2 heteroatoms selected from O, S and N;

$R^2$ is hydrogen or $C_1$–$C_6$ alkyl optionally substituted by 1 to 3 substituents independently selected from halo, $C_1$–$C_4$ alkoxy, —$NR^6R^6$, and —$SO_2R^5$;

n is 1 or 2 and each $R^3$ is independently selected from hydrogen, halo, hydroxy, $C_1$–$C_6$ alkyl, —$NR^6R^6$, and $C_1$–$C_4$ alkoxy, wherein the alkyl moieties of said $R^3$ groups are optionally substituted by 1 to 3 substituents independently selected from halo, $C_1$–$C_4$ alkoxy, —$NR^6R^6$, and —$SO_2R^5$; and, $R^4$ is azido or -(ethynyl)-$R^{11}$ wherein $R^{11}$ is hydrogen or $C_1$–$C_6$ alkyl optionally substituted by hydroxy, —$OR^6$, or —$NR^6R^6$.

Preferred compounds of formula I include those wherein $R^2$ is hydrogen and $R^4$ is -(ethynyl)-$R^{11}$.

Other preferred compounds of formula I include those wherein m is 1 or 2;

each $R^1$ is independently selected from the group consisting of hydrogen, hydroxy, hydroxyamino, carboxy, nitro, carbamoyl, ureido, $R^5$ optionally substituted with halo, —$OR^6$, carboxy, —$C(O)NR^6R^6$, A or —$NR^6R^6$; —$OR^5$ optionally substituted with halo, —$OR^6$, —$OC(O)R^6$, —$NR^6R^6$, or A; —$NR^6R^6$, —$C(O)R^6R^5$, —$SR^5$, phenyl-$(C_2-C_4)$-alkoxy, cyano, phenyl; —$NHR^5$ optionally substituted with halo or $R^9$ wherein said $R^9$ is optionally substituted by $R^9$; —$NHOR^5$, —$SR^5$, $C_1-C_4$ alkylsulfonylamino, phthalimido-$(C_1-C_4)$-alkylsulfonylamino, 3-phenylureido, 2-oxopyrrolidin-1-yl, 2,5-dioxopyrrolidin-1-yl, halo-$(C_2-C_4)$-alkanoylamino, hydroxy-$(C_2-C_4)$-alkanoylamino, $(C_2-C_4)$-alkanoyloxy-$(C_2-C_4)$-alkanoylamino, $(C_1-C_4)$-alkoxy-$(C_2-C_4)$-alkanoylamino, $(C_1-C_4)$-alkoxycarbonyl-$(C_2-C_4)$-alkanoylamino, carbamoyl-$(C_2-C_4)$-alkanoylamino, N-$(C_1-C_4)$-alkylcarbamoyl-$(C_2-C_4)$-alkanoylamino, N,N-di-[$(C_1-C_4)$-alkyl]carbamoyl-$(C_2-C_4)$-alkanoylamino, amino-$(C_2-C_4)$-alkanoylamino, $(C_1-C_4)$-alkyl-amino-$(C_2-C_4)$-alkanoylamino, and di-$(C_1-C_4)$-alkyl-amino-$(C_2-C_4)$-alkanoylamino, and wherein said phenyl or phenoxy or anilino substituent in the foregoing $R^1$ groups is optionally substituted with one or two substituents independently selected from halo, $C_1-C_4$ alkyl and $C_1-C_4$ alkoxy;

each $R^3$ is independently selected from hydrogen, methyl, ethyl, amino, halo and hydroxy; and, $R^4$ is ethynyl.

Other preferred compounds of formula I include those wherein each $R^1$ is independently selected from hydrogen, hydroxy, hydroxyamino, nitro, carbamoyl, ureido, $R^5$ optionally substituted with halo, —$OR^6$, carboxy, or —$C(O)NH_2$; —$OR^5$ optionally substituted with halo, —$OR^6$, —$OC(O)R^6$, —$NR^6R^6$, or A; —$NR^6R^6$, —$C(O)NR^6R^6$, —$SR^5$, phenyl-$(C_2-C_4)$-alkoxy wherein said phenyl moiety is optionally substituted with 1 or 2 substituents independently selected from halo, $R^5$ or —$OR^5$.

Other preferred compounds of formula I include those wherein $R^2$ is hydrogen and $R^4$ is azido.

Other preferred compounds of formula I include those wherein $R^3$ is halo and $R^1$ is hydrogen or —$OR^5$.

Other preferred compounds of formula I include those wherein $R^1$ is methoxy.

Specific preferred compounds of formula I include the following:

(6,7-dimethoxyquinazolin-4-yl)-(3-ethynylphenyl)-amine;
(6,7-dimethoxyquinazolin-4-yl)-[3-(3'-hydroxypropyn-1-yl) phenyl]-amine;
[3-(2'-(aminomethyl)-ethynyl)phenyl]-(6,7-dimethoxyquinazolin-4-yl)-amine;
(3-ethynylphenyl)-(6-nitroquinazolin-4-yl)-amine;
(6,7-dimethoxyquinazolin-4-yl)-(4-ethynylphenyl)-amine;
(6,7-dimethoxyquinazolin-4-yl)-(3-ethynyl-2-methylphenyl)-amine;
(6-aminoquinazolin-4-yl)-(3-ethynylphenyl)-amine;
(3-ethynylphenyl)-(6-methanesulfonylaminoquinazolin-4-yl)-amine;
(3-ethynylphenyl)-(6,7-methylenedioxyquinazolin-4-yl)-amine;
(6,7-dimethoxyquinazolin-4-yl)-(3-ethynyl-6-methylphenyl)-amine;
(3-ethynylphenyl)-(7-nitroquinazolin-4-yl)-amine;
(3-ethynylphenyl)-[6-(4'-toluenesulfonylamino)quinazolin-4-yl]-amine;
(3-ethynylphenyl)-{6-[2'-phthalimido-eth-1'-yl-sulfonylamino]quinazolin-4-yl}-amine;
(3-ethynylphenyl)-(6-guanidinoquinazolin-4-yl)-amine;
(7-aminoquinazolin-4-yl)-(3-ethynylphenyl)-amine;
(3-ethynylphenyl)-(7-methoxyquinazolin-4-yl)-amine;
(6-carbomethoxyquinazolin-4-yl)-(3-ethynylphenyl)-amine;
(7-carbomethoxyquinazolin-4-yl)-(3-ethynylphenyl)-amine;
[6,7-bis(2-methoxyethoxy)quinazolin-4-yl]-(3-ethynylphenyl)-amine;
(3-azidophenyl)-(6,7-dimethoxyquinazolin-4-yl)-amine;
(3-azido-5-chlorophenyl)-(6,7-dimethoxyquinazolin-4-yl)-amine;
(4-azidophenyl)-(6,7-dimethoxyquinazolin-4-yl)-amine;
(3-ethynylphenyl)-(6-methansulfonyl-quinazolin-4-yl)-amine;
(6-ethansulfanyl-quinazolin-4-yl)-(3-ethynylphenyl)-amine
(6,7-dimethoxy-quinazolin-4-yl)-(3-ethynyl-4-fluoro-phenyl)-amine;
(6,7-dimethoxy-quinazolin-4-yl)-[3-(propyn-1'-yl)-phenyl]-amine;
[6,7-bis-(2-methoxy-ethoxy)-quinazolin-4-yl]-(5-ethynyl-2-methyl-phenyl)-amine;
[6,7-bis-(2-methoxy-ethoxy)-quinazolin-4-yl]-(3-ethynyl-4-fluoro-phenyl)-amine;
[6,7-bis-(2-chloro-ethoxy)-quinazolin-4-yl]-(3-ethynyl-phenyl)-amine;
[6-(2-chloro-ethoxy)-7-(2-methoxy-ethoxy)-quinazolin-4-yl]-(3-ethynyl-phenyl)-amine;
[6,7-bis-(2-acetoxy-ethoxy)-quinazolin-4-yl]-(3-ethynyl-phenyl)-amine;
2-[4-(3-ethynyl-phenylamino)-7-(2-hydroxy-ethoxy)-quinazolin-6-yloxy]-ethanol;
[6-(2-acetoxy-ethoxy)-7-(2-methoxy-ethoxy)-quinazolin-4-yl]-(3-ethynyl-phenyl)-amine;
[7-(2-chloro-ethoxy)-6-(2-methoxy-ethoxy)-quinazolin-4-yl]-(3-ethynyl-phenyl)-amine;
[7-(2-acetoxy-ethoxy)-6-(2-methoxy-ethoxy)-quinazolin-4-yl]-(3-ethynyl-phenyl)-amine;
2-[4-(3-ethynyl-phenylamino)-6-(2-hydroxy-ethoxy)-quinazolin-7-yloxy]-ethanol;
2-[4-(3-ethynyl-phenylamino)-7-(2-methoxy-ethoxy)-quinazolin-6-yloxy]-ethanol;
2-[4-(3-ethynyl-phenylamino)-6-(2-methoxy-ethoxy)-quinazolin-7-yloxy]-ethanol;
[6-(2-acetoxy-ethoxy)-7-(2-methoxy-ethoxy)-quinazolin-4-yl]-(3-ethynyl-phenyl)-amine;
(3-ethynyl-phenyl)-{6-(2-methoxy-ethoxy)-7-[2-(4methyl-piperazin-1-yl)-ethoxy]-quinazolin-4-yl}-amine;
(3-ethynyl-phenyl)-[7-(2-methoxy-ethoxy)-6-(2-morpholin-4-yl)-ethoxy)-quinazolin-4-yl]-amine;
(6,7-diethoxyquinazolin-1-yl)-(3-ethynylphenyl)-amine;
(6,7-dibutoxyquinazolin-1-yl)-(3-ethynylphenyl)-amine;
(6,7-diisopropoxyquinazolin-1-yl)-(3-ethynylphenyl)-amine;
(6,7-diethoxyquinazolin-1-yl)-(3-ethynyl-2-methyl-phenyl)-amine;
[6,7-bis-(2-methoxy-ethoxy)-quinazolin-1-yl]-(3-ethynyl-2-methyl-phenyl)-amine;
(3-ethynylphenyl)-[6-(2-hydroxy-ethoxy)-7-(2-methoxy-ethoxy)-quinazolin-1-yl]-amine;
[6,7-bis-(2-hydroxy-ethoxy)-quinazolin-1-yl]-(3-ethynylphenyl)-amine; and
2-[4-(3-ethynyl-phenylamino)-6-(2-methoxy-ethoxy)-quinazolin-7-yloxy]-ethanol.

Other specific preferred compounds of formula I include the following:

(6,7-dipropoxy-quinazolin-4-yl)-(3-ethynyl-phenyl)-amine;

(6.7-diethoxy-quinazolin-4-yl)-(3-ethynyl-5-fluoro-phenyl)-amine;

(6.7-diethoxy-quinazolin-4-yl)-(3-ethynyl-4-fluoro-phenyl)-amine;

(6.7-diethoxy-quinazolin-4-yl)-(5-ethynyl-2-methyl-phenyl)-amine;

(6.7-diethoxy-quinazolin-4-yl)-(3-ethynyl-4-methyl-phenyl)-amine;

(6-aminomethyl-7-methoxy-quinazolin-4-yl)-(3-ethynyl-phenyl)-amine;

(6-aminomethyl-7-methoxy-quinazolin-4-yl)-(3-ethynylphenyl)-amine;

(6-aminocarbonylmethyl-7-methoxy-quinazolin-4-yl)-(3-ethynylphenyl)-amine;

(6-aminocarbonylethyl-7-methoxy-quinazolin-4-yl)-(3-ethynylphenyl)-amine;

(6-aminocarbonylmethyl-7-ethoxy-quinazolin-4-yl)-(3-ethynylphenyl)-amine;

(6-aminocarbonylethyl-7-ethoxy-quinazolin-4-yl)-(3-ethynylphenyl)-amine;

(6-aminocarbonylmethyl-7-isopropoxy-quinazolin-4-yl)-(3-ethynylphenyl)-amine;

(6-aminocarbonylmethyl-7-propoxy-quinazolin-4-yl)-(3-ethynylphenyl)-amine;

(6-aminocarbonylmethyl-7-methoxy-quinazolin-4-yl)-(3-ethynylphenyl)-amine;

(6-aminocarbonylethyl-7-isopropoxy-quinazolin-4-yl)-(3-ethynylphenyl)-amine; and (6-aminocarbonylethyl-7-propoxy-quinazolin-4-yl)-(3-ethynylphenyl)-amine.

Other specific preferred compounds of formula I include the following:

(6.7-diethoxyquinazolin-1-yl)-(3-ethynylphenyl)-amine;

(3-ethynylphenyl)-[6-(2-hydroxy-ethoxy)-7-(2-methoxy-ethoxy)-quinazolin-1-yl]-amine;

[6,7-bis-(2-hydroxy-ethoxy)-quinazolin-1-yl]-(3-ethynylphenyl)-amine;

[6,7-bis-(2-methoxy-ethoxy)-quinazolin-1-yl]-(3-ethynylphenyl)-amine;

(6,7-dimethoxyquinazolin-1-yl)-(3-ethynylphenyl)-amine;

(3-ethynylphenyl)-(6-methanesulfonylamino-quinazolin-1-yl)-amine; and, (6-amino-quinazolin-1-yl)-(3-ethynylphenyl)-amine.

The invention further relates to a pharmaceutical composition for the treatment of a hyperproliferative disorder in a mammal which comprises a therapeutically-effective amount of the compound of claim 1 and a pharmaceutically acceptable carrier.

The invention further relates to a method of treating a hyperproliferative disorder in a mammal which comprises administering to said mammal a therapeutically-effective amount of the compound of claim 1.

In a preferred embodiment, the method of treating hyperproliferative disorders includes those wherein said hyperproliferative disorder is cancer.

In another preferred embodiment, the method of treating hyperproliferative disorders includes those wherein said hyperproliferative disorder is said cancer is brain, lung, squamous cell, bladder, gastric, pancreatic, breast, head, neck, oesophageal, gynecological or thyroid cancer.

In another preferred embodiment, the method of treating hyperproliferative disorders includes those wherein said hyperproliferative disorder is noncancerous.

In another preferred embodiment, the method of treating hyperproliferative disorders includes those wherein said hyperproliferative disorder is a benign hyperplasia of the skin or prostate.

The invention further relates to a process for preparing a compound of the formula

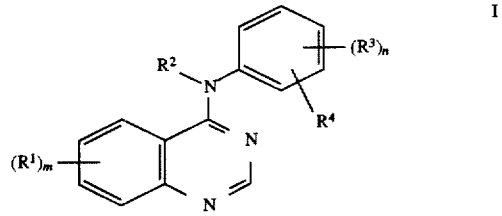

or a pharmaceutically acceptable salt or prodrug thereof, wherein:

m is 1, 2, or 3;

each $R^1$ is independently selected from the group consisting of hydrogen, halo, hydroxy, hydroxyamino, carboxy, nitro, guanidino, ureido, cyano, trifluoromethyl, and -($C_1$-$C_4$ alkylene)-W-(phenyl) wherein W is a single bond, O, S or NH;

or each $R^1$ is independently selected from $R^9$ and ($C_1$-$C_4$)-alkyl substituted by cyano, wherein $R^9$ is selected from the group consisting of $R^5$, —$OR^6$, —$NR^6R^6$, —$C(O)R^7$, —$NHOR^5$, —$OC(O)R^6$, cyano, A and —$YR^5$; $R^5$ is $C_1$-$C_4$ alkyl; $R^6$ is independently hydrogen or $R^5$; $R^7$ is $R^5$, —$OR^6$ or —$NR^6R^6$; A is selected from piperidino, morpholino, pyrrolidino, 4-$R^6$-piperazin-1-yl, imidazol-1-yl, 4-pyridon-1-yl, -($C_1$-$C_4$ alkylene)($CO_2H$), phenoxy, phenyl, phenylsulfanyl, $C_2$-$C_4$ alkenyl, and -($C_1$-$C_4$ alkylene)$C(O)NR^6R^6$; and Y is S, SO, or $SO_2$; wherein the alkyl moieties in $R^5$, —$OR^6$ and —$NR^6R^6$ are optionally substituted by one to three substituents independently selected from halo and $R^9$, and wherein the alkyl moieties of said optional substituents are optionally substituted by halo or $R^9$, with the proviso that two heteroatoms are not attached to the same carbon atom, and with the further proviso that no more than three $R^9$ groups may comprise a single $R^1$ group;

or each $R^1$ is independently selected from —$NHSO_2R^5$, phthalimido-($C_1$-$C_4$)-alkylsulfonylamino, benzamido, benzenesulfonylamino, 3-phenylureido, 2-oxopyrrolidin-1-yl, 2,5-dioxopyrrolidin-1-yl, and $R^{10}$-($C_2$-$C_4$)-alkanoylamino wherein $R^{10}$ is selected from halo, —$OR^6$, $C_2$-$C_4$ alkanoyloxy, —$C(O)R^7$, and —$NR^6R^6$; and wherein the foregoing $R^1$ groups are optionally substituted by 1 or 2 substituents independently selected from halo, $C_1$-$C_4$ alkyl, cyano, methanesulfonyl and $C_1$-$C_4$ alkoxy;

or two $R^1$ groups are taken together with the carbons to which they are attached to form a 5–8 membered ring that includes 1 or 2 heteroatoms selected from O, S and N;

$R^2$ is hydrogen or $C_1$-$C_6$ alkyl optionally substituted by 1 to 3 substituents independently selected from halo, $C_1$-$C_4$ alkoxy, —$NR^6R^6$, and —$SO_2R^5$;

n is 1 or 2 and each $R^3$ is independently selected from hydrogen, halo, hydroxy, $C_1$-$C_6$ alkyl, —$NR^6R^6$, and $C_1$-$C_4$ alkoxy, wherein the alkyl moieties of said $R^3$ groups are optionally substituted by 1 to 3 substituents independently selected from halo, $C_1$-$C_4$ alkoxy, —$NR^6R^6$, and —$SO_2R^5$; and, $R^4$ is azido or -(ethynyl)-$R^{11}$ wherein $R^{11}$ is hydrogen or $C_1$-$C_6$ alkyl optionally substituted by hydroxy, —$OR^6$, or —$NR^6R^6$; which comprises a) treating a compound of the formula

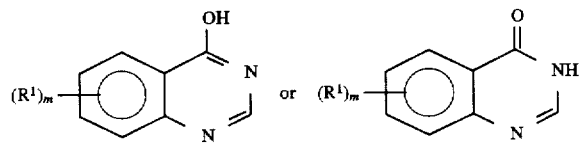

wherein $R^1$ and m are as defined above, with $CCl_4$ and $(C_6$–$C_{10}aryl)_3P$, optionally supported on an inert polymer, wherein the aryl moieties of said $(C_6$–$C_{10}aryl)_3P$ are optionally substituted by $C_1$–$C_6$ alkyl; and b) treating the product of step a) with a compound of the formula

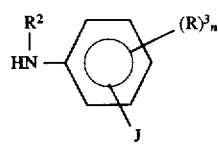

wherein $R^2$, $R^3$ and n are as defined above, and J is Y or $R^4$, wherein $R^4$ is as defined above and wherein Y is $NH_2$, Br, I or trifluoromethanesulfonyloxy, with the proviso that when J is Y then the product of step b) must further be treated with an alkyne where Y is Br, I or trifluoromethanesulfonyloxy, or an azide where Y is $NH_2$.

Preferred processes for preparing the compound of formula I include those wherein each aryl group is selected from phenyl, naphth-1-yl and naphth-2-yl.

Other preferred processes for preparing the compound of formula I include those wherein each Ar in $(C_6$–$C_{10}aryl)_3P$ is phenyl.

Other preferred processes for preparing the compound of formula I include those wherein said $(C_6$–$C_{10}aryl)_3P$ is supported on an inert polymer.

Other preferred processes for preparing the compound of formula I include those wherein said inert polymer is a divinylbenzene-cross-linked polymer of styrene.

The term "halo", as used herein, unless otherwise indicated, means chloro, bromo, iodo, or fluoro.

The term "alkyl", as used herein, unless otherwise indicated, means straight chained, cyclic or branched, saturated or unsaturated hydrocarbon moiety with the proviso that said alkyl must comprise three or more carbon atoms if it is branched or cyclic.

As used herein, the expression "reaction-inert solvent" refers to a solvent which does not interact with starting materials, reagents, intermediates or products in a manner which adversely affects the yield of the desired product.

Other features and advantages will be apparent from the specification and claims which describe the invention.

SCHEME

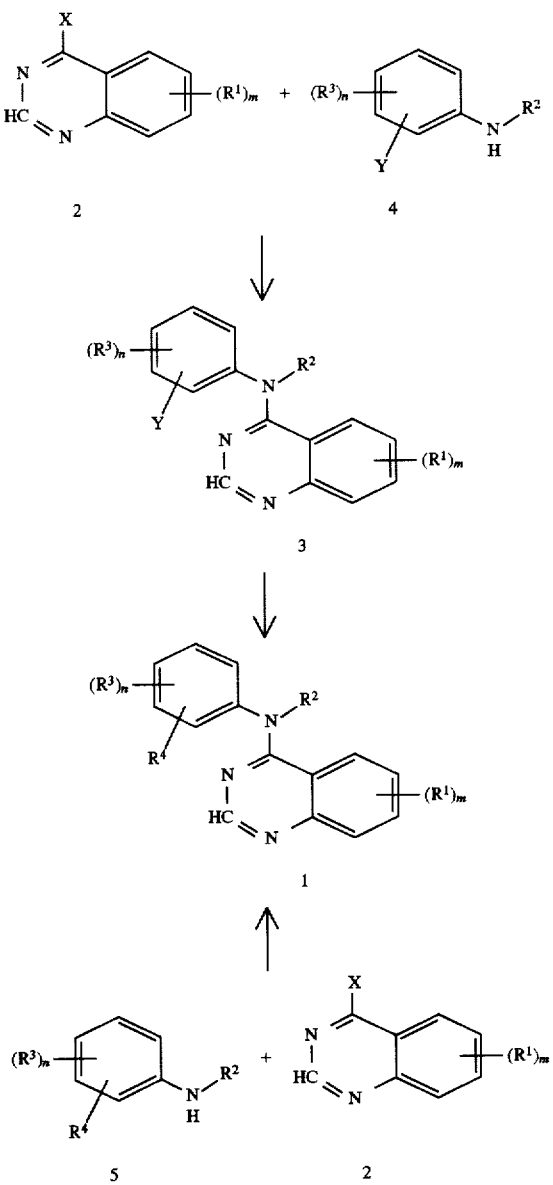

DETAILED DESCRIPTION OF THE INVENTION

The Formula I compounds, pharmaceutically acceptable salts and prodrugs thereof (hereafter the active compounds) may be prepared by any process known to be applicable to the preparation of chemically-related compounds.

In general the active compounds may be made from the appropriately substituted quinazoline using the appropriately substituted amine.

As shown in the Scheme the appropriate 4-substituted quinazoline 2 wherein X is a suitable displaceable leaving group such as halo, aryloxy, alkylsulfinyl, alkylsulfonyl such as trifluoromethanesulfonyloxy, arylsulfinyl, arylsulfonyl, siloxy, cyano, pyrazolo, triazolo or tetrazolo, preferably a 4-chloroquinazoline, is reacted with the appropriate amine or amine hydrochloride 4 or 5, wherein $R^4$ is as described above and Y is Br, I, or trifluoromethane-sulfonyloxy in a solvent such as a ($C_1$–$C_6$)alcohol, dimethylformamide (DMF), N-methylpyrrolidin-2-one, chloroform, acetonitrile, tetrahydrofuran (THF), 1–4 dioxane, pyridine or other aprotic solvent. The reaction may be effected in the presence of a base, preferably an alkali or alkaline earth metal carbonate or hydroxide or a tertiary amine base, such as pyridine, 2,6-lutidine, collidine, N-methyl-morpholine, triethylamine, 4-dimethylamino-pyridine or N,N-dimethylaniline. These bases are hereinafter refered to as suitable bases. The reaction mixture is maintained at a temperature from about ambient to about the reflux temperature of the solvent, preferably from about 35° C. to about reflux, until substantially no remaining 4-haloquinazoline can be detected, typically about 2 to about 24 hours. Preferably, the reaction is performed under an inert atmosphere such as dry nitrogen.

Generally the reactants are combined stoichiometrically. When an amine base is used for those compounds where a salt (typically the HCl salt) of an amine 4 or 5 is used, it is preferable to use excess amine base, generally an extra equivalent of amine base. (Alternatively, if an amine base is not used an excess of the amine 4 or 5 may be used).

For those compounds where a sterically hindered amine 4 (such as a 2-alkyl-3-ethynylaniline) or very reactive 4-haloquinazoline is used it is preferable to use t-butyl alcohol or a polar aprotic solvent such as DMF or N-methylpyrrolidin-2-one as the solvent.

Alternatively, a 4-substituted quinazoline 2 wherein X is hydroxyl or oxo (and the 2-nitrogen is hydrogenated) is reacted with carbon tetrachloride and an optionally substituted triarylphosphine which is optionally supported on an inert polymer (e.g. triphenylphosphine, polymer supported, Aldrich Cat. No. 36,645-5, which is a 2% divinylbenzene cross-linked polystyrene containing 3 mmol phosphorous per gram resin) in a solvent such as carbon tetrachloride, chloroform, dichloroethane, tetrahydrofuran, acetonitrile or other aprotic solvent or mixtures thereof. The reaction mixture is maintained at a temperature from about ambient to reflux, preferably from about 35° C. to reflux, for 2 to 24 hours. This mixture is reacted with the appropriate amine or amine hydrochloride 4 or 5 either directly or after removal of solvent, for example by vacuum evaporation, and addition of a suitable alternative solvent such as a ($C_1$–$C_6$) alcohol, DMF, N-methylpyrrolidin-2-one, pyridine or 1–4 dioxane. Then, the reaction mixture is maintained at a temperature from about ambient to the reflux temperature of the solvent preferably from about 35° C. to about reflux, until substantially complete formation of product is acheived, typically from about 2 to about 24 hours. Preferably the reaction is performed under an inert atmosphere such as dry nitrogen.

When compound 4, wherein Y is Br, I, or trifluoromethanesulfonyloxy, is used as starting material in the reaction with quinazoline 2, a compound of formula 3 is formed wherein $R^1$, $R^2$, $R^3$, and Y are as described above. Compound 3 is converted to compounds of formula 1 wherein $R^4$ is $R^{11}$ethynyl, and $R^{11}$ is as defined above, by reaction with a suitable palladium reagent such as tetrakis (triphenylphosphine)palladium or bis(triphenylphosphine) palladium dichloride in the presence of a suitable Lewis acid such as cuprous chloride and a suitable alkyne such as trimethylsilylacetylene, propargyl alcohol or 3-(N,N-dimethylamino)-propyne in a solvent such as diethylamine or triethylamine. Compounds 3, wherein Y is $NH_2$, may be converted to compounds 1 wherein $R^4$ is azide by treatment of compound 3 with a diazotizing agent, such as an acid and a nitrite (e.g., acetic acid and $NaNO_2$) followed by treatment of the resulting product with an azide, such as $NaN_3$.

For the production of those compounds of Formula I wherein an $R^1$ is an amino or hydroxyamino group the reduction of the corresponding Formula I compound wherein $R^1$ is nitro is employed.

The reduction may conveniently be carried out by any of the many procedures known for such transformations. The reduction may be carried out, for example, by hydrogenation of the nitro compound in a reaction-inert solvent in the presence of a suitable metal catalyst such as palladium, platinum or nickel. A further suitable reducing agent is, for example, an activated metal such as activated iron (produced by washing iron powder with a dilute solution of an acid such as hydrochloric acid). Thus, for example, the reduction may be carried out by heating a mixture of the nitro compound and the activated metal with concentrated hydrochloric acid in a solvent such as a mixture of water and an alcohol, for example, methanol or ethanol, to a temperature in the range, for example, 50° to 150° C., conveniently at or near 70° C. Another suitable class of reducing agents are the alkali metal dithionites, such as sodium dithionite, which may be used in ($C_1$–$C_4$)alkanoic acids, ($C_1$–$C_6$)alkanols, water or mixtures thereof.

For the production of those compounds of Formula I wherein $R^2$ or $R^3$ incorporates a primary or secondary amino moiety (other than the amino group intended to react with the quinazoline), such free amino group is preferably protected prior to the above described reaction followed by deprotection, subsequent to the above described reaction with 4-(substituted)quinazoline 2.

Several well known nitrogen protecting groups can be used. Such groups include ($C_1$–$C_6$)alkoxycarbonyl, optionally substituted benzyloxycarbonyl, aryloxycarbonyl, trityl, vinyloxycarbonyl, O-nitrophenylsulfonyl, diphenylphosphinyl, p-toluenesulfonyl, and benzyl. The addition of the nitrogen protecting group may be carried out in a chlorinated hydrocarbon solvent such as methylene chloride or 1,2-dichloroethane, or an ethereal solvent such as glyme, diglyme or THF, in the presence or absence of a tertiary amine base such as triethylamine, diisopropylethylamine or pyridine, preferably triethylamine, at a temperature from about 0° C. to about 50° C., preferably about ambient temperature. Alternatively, the protecting groups are , conveniently attached using Schotten-Baumann conditions.

Subsequent to the above described coupling reaction, of compounds 2 and 5, the protecting group may be removed by deprotecting methods known to those skilled in the art such as treatment with trifluoroacetic acid in methylene chloride for the tert-butoxycarbonyl protected products.

For a description of protecting groups and their use, see T. W. Greene and P. G. M. Wuts, "Protective Groups in Organic Synthesis" Second Ed., John Wiley & Sons, New York, 1991.

For the production of compounds of Formula I wherein $R^1$ or $R^2$ is hydroxy, cleavage of a Formula I compound wherein $R^1$ or $R^2$ is ($C_1$–$C_4$)alkoxy is preferred.

The cleavage reaction may conveniently be carried out by any of the many procedures known for such a transformation. Treatment of the protected formula I derivative with molten pyridine hydrochloride (20–30 eq.) at 150° to 175° C. may be employed for O-dealkylations. Alternatively, the cleavage reaction may be carried out, for example, by treatment of the protected quinazoline derivative with an alkali metal ($C_1$–$C_4$)alkylsulphide, such as sodium ethanethiolate or by treatment with an alkali metal diarylphosphide such as lithium diphenylphosphide. The cleavage reaction may also, conveniently, be carried out by treatment of the protected quinazoline derivative with a boron or aluminum trihalide such as boron tribromide. Such reactions are preferably carried out in the presence of a reaction-inert solvent at a suitable temperature.

Compounds of formula I, wherein $R^1$ or $R^2$ is a ($C_1$–$C_4$) alkylsulphinyl or ($C_1$–$C_4$)alkylsulphonyl group are preferably prepared by oxidation of a formula I compound wherein $R^1$ or $R^2$ is a ($C_1$–$C_4$)alkylsulfanyl group. Suitable oxidizing agents are known in the art for the oxidation of sulfanyl to sulphinyl and/or sulphonyl, e.g., hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible using the stoichiometric amount of oxidizing agent in order to reduce the risk of over oxidation and damage to other functional groups. In general, the reaction is carried out in a suitable solvent such as methylene chloride, chloroform, acetone, tetrahydrofuran or tert-butyl methyl ether and at a temperature from about −25° to 50° C., preferably at or near ambient temperature, i.e., in the range of 15° to 35° C. When a compound carrying a sulphinyl group is desired a milder oxidizing agents should be used such as sodium or potassium metaperiodate, conveniently in a polar solvent such as acetic acid or ethanol. The compounds of formula I containing a ($C_1$–$C_4$)alkylsulphonyl group may be obtained by oxidation of the corresponding ($C_1$–$C_4$)alkylsulphinyl compound as well as of the corresponding ($C_1C_4$)alkylsulfanyl compound.

Compounds of formula I wherein $R^1$ is optionally substituted ($C_2$–$C_4$)alkanoylamino, ureido, 3-phenylureido, benzamido or sulfonamido can be prepared by acylation or sulfonylation of a corresponding compound wherein $R^1$ is amino. Suitable acylating agents are any agents known in the art for the acylation of amino to acylamino, for example, acyl halides, e.g., a ($C_2$–$C_4$)alkanoyl chloride or bromide or a benzoyl chloride or bromide, alkanoic acid anhydrides or mixed anhydrides (e.g., acetic anhydride or the mixed anhydride formed by the reaction of an alkanoic acid and a ($C_1$–$C_4$)alkoxycarbonyl halide, for example ($C_1$–$C_4$) alkoxycarbonyl chloride, in the presence of a suitable base. For the production of those compounds of Formula I wherein $R^1$ is ureido or 3-phenylureido, a suitable acylating agent is, for example, a cyanate, e.g., an alkali metal cyanate such as sodium cyanate, or an isocyanate such as phenyl isocyanate. N-sulfonylations may be carried out with suitable sulfonyl halides or sulfonylanhydrides in the presence of a tertiary amine base. In general the acylation or sulfonylation is carried out in a reaction-inert solvent and at a temperature in the range of about −30° to 120° C., conveniently at or near ambient temperature.

Compounds of Formula I wherein $R^1$ is ($C_1$–$C_4$)alkoxy or substituted ($C_1$–$C_4$)alkoxy or $R^1$ is ($C_1$–$C_4$)alkylamino or substituted mono-N- or di-N,N-($C_1$–$C_4$)alkylamino, are prepared by the alkylation, preferably in the presence of a suitable base, of a corresponding compound wherein $R^1$ is hydroxy or amino, respectively. Suitable alkylating agents include alkyl or substituted alkyl halides, for example, an optionally substituted ($C_1$–$C_4$)alkyl chloride, bromide or iodide, in the presence of a suitable base in a reaction-inert solvent and at a temperature in the range of about 10° to 140° C., conveniently at or near ambient temperature.

For the production of those compounds of Formula I wherein $R^1$ is an amino-, oxy- or cyano-substituted ($C_1$–$C_4$)alkyl substituent, a corresponding compound wherein $R^1$ is a ($C_1$–$C_4$)alkyl substituent bearing a group which is displacable by an amino-, alkoxy-, or cyano group is reacted with an appropriate amine, alcohol or cyanide, preferably in the presence of a suitable base. The reaction is preferably carried out in a reaction-inert solvent or diluent and at a temperature in the range of about 10° to 100° C., preferably at or near ambient temperature.

Compounds of Formula I, wherein $R^1$ is a carboxy substituent or a substituent which includes a carboxy group are prepared by hydrolysis of a corresponding compound wherein $R^1$ is a ($C_1$–$C_4$)alkoxycarbonyl substituent or a substituent which includes a ($C_1$–$C_4$)alkoxycarbonyl group. The hydrolysis may conveniently be performed, for example, under basic conditions, e.g., in the presence of alkali metal hydroxide as illustrated in the accompanying Examples.

Compounds of Formula I wherein $R^1$ is amino, ($C_1$–$C_4$) alkylamino, di-[($C_1$–$C_4$)alkyl]amino, pyrrolidin-1-yl, piperidino, morpholino, piperazin-1-yl, 4-($C_1$–$C_4$) alkylpiperazin-1-yl or ($C_1$–$C_4$)alkysulfanyl, may be prepared by the reaction, in the presence of a suitable base, of a corresponding compound wherein $R^1$ is an amine or thiol displaceable group with an appropriate amine or thiol. The reaction is preferably carried out in a reaction-inert solvent or diluent and at a temperature in the range of about 10° to 180° C., conveniently in the range 100° to 150° C.

Compounds of Formula I wherein $R^1$ is 2-oxopyrrolidin-1-yl or 2-oxopiperidin-1-yl are prepared by the cyclisation, in the presence of a suitable base, of a corresponding compound wherein $R^1$ is a halo-($C_2$–$C_4$)alkanoylamino group. The reaction is preferably carried out in a reaction-inert solvent or diluent and at a temperature in the range of about 10° to 100° C., conveniently at or near ambient temperature.

For the production of compounds of Formula I in which $R^1$ is carbamoyl, substituted carbamoyl, alkanoyloxy or substituted alkanoyloxy, the carbamoylation or acylation of a corresponding compound wherein $R^1$ is hydroxy is convenient.

Suitable acylating agents known in the art for acylation of hydroxyaryl moieties to alkanoyloxyaryl groups include, for example, ($C_2$–$C_4$)alkanoyl halides, ($C_2$–$C_4$)alkanoyl anhydrides and mixed anhydrides as described above, and suitable substituted derivatives thereof may be employed, typically in the presence of a suitable base. Alternatively, ($C^2$–$C_4$)alkanoic acids or suitably substituted derivatives thereof may be coupled with a Formula I compound wherein $R^1$ is hydroxy with the aid of a condensing agent such as a carbodiimide. For the production of those compounds of Formula I in which $R^1$ is carbamoyl or substituted carbamoyl, suitable carbamoylating agents are, for example, cyanates or alkyl or arylisocyanates, typically in the presence of a suitable base. Alternatively, suitable intermediates such as the chloroformate or carbonylimidazolyl derivative of a compound of Formula I in which $R^1$ is hydroxy may be generated, for example, by treatment of said derivative with phosgene (or a phosgene equivalent) or carbonyidiimidazole. The resulting intermediate may then be reacted with an appropriate amine or substituted amine to produce the desired carbamoyl derivatives.

Compounds of formula I wherein $R^1$ is aminocarbonyl or a substituted aminocarbonyl can be prepared by the aminolysis of a suitable intermediate in which $R^1$ is carboxy.

The activation and coupling of formula I compounds wherein $R^1$ is carboxy may be performed by a variety of methods known to those skilled in the art. Suitable methods include activation of the carboxyl as an acid halide, azide, symmetric or mixed anhydride, or active ester of appropriate reactivity for coupling with the desired amine. Examples of such types of intermediates and their production and use in couplings with amines may be found extensively in the literature; for example M. Bodansky and A. Bodansky, "The Practice of Peptide Synthesis", Springer,-Verlag, New York, 1984. The resulting formula I compounds may be isolated and purified by standard methods, such as solvent removal and recrystallization or chromatography.

The starting materials for the above described reaction schemes (e.g., amines, quinazolines and amine protecting groups) are readily available or can be easily synthesized by those skilled in the art using conventional methods of organic synthesis. For example, the preparation of 2,3-dihydro-1,4-benzoxazine derivatives are described in R. C. Elderfield, W. H. Todd, S. Gerber, Ch. 12 in "Heterocyclic Compounds", Vol. 6, R. C. Elderfield ed., John Wiley and Sons, Inc., N.Y., 1957. Substituted 2,3-dihydrobenzothiazinyl compounds are described by R. C. Elderfield and E. E. Harris in Ch. 13 of Volume 6 of the Elderfield "Heterocyclic Compounds" book.

Certain Formula I quinazolines can exist in solvated, as well as unsolvated forms, such as the hydrated forms. It is to be understood that the invention encompasses all such solvated, as well as unsolvated forms, which possess activity against hyperproliferative diseases.

A suitable pharmaceutically-acceptable salt of a compound of formula I is, for example, an acid-addition salt of a corresponding compound which is sufficiently basic, e.g., an acid-addition salt with, for example, an inorganic or organic acid such as hydrochloric, hydrobromic, sulphuric, phosphoric, methanesulfonic, benzenesulfonic, trifluoroacetic, citric, lactic or maleic acid. A suitable pharmaceutically-acceptable base-addition salt of a compound of formula I which is acidic is an alkali metal salt, for example, a lithium, sodium or potassium salt; an alkaline earth metal salt, for example, a calcium or magnesium salt; an ammonium salt; or a salt with an organic base which affords a physiologically-acceptable cation for example a salt with methylamine, dimethylamine, trimethylamine, piperidine, morpholine or tris-(2-hydroxyethyl)amine. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered by filtration; by precipitation with a non-solvent, preferably an etheral or hydrocarbon solvent, followed by filtration and by evaporation of a solvent, or, in the case of aqueous solutions, by lyophilization.

Some of the compounds of Formula I have asymmetric carbon atoms. Such diasteromeric mixtures can be separated into their individual diastereomers on the basis of their physical chemical differences by methods known per se., for example, by chromatography and/or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomers mixtures and pure enantiomers are considered as part of the invention.

The active compounds of this invention are potent inhibitors of the erbB family of oncogenic and protooncogenic protein tyrosine kinases such as epidermal growth factor receptor (EGFR), erbB2, HER3, or HER4 and thus are all adapted to therapeutic use as antiproliferative agents (e.g., anticancer) in mammals, particularly humans. In particular, the compounds of this invention are therapeutants or prophylactics for the treatment of a variety of human tumors (renal, liver, kidney, bladder, breast, gastric, ovarian, colorectal, prostate, pancreatic, lung, vulval, thyroid, hepatic carcinomas, sarcomas, glioblastomas, various head and neck tumors), and other hyperplastic conditions such as benign hyperplasia of the skin (e.g., psoriasis) or prostate (e.g., BPH). It is, in addition, expected that a quinazoline of the present invention may possess activity against a range of leukemias and lymphoid malignancies.

The active compounds may also be expected to be useful in the treatment of additional disorders in which aberrant expression ligand/receptor interactions, activation or signalling events related to various protein tyrosine kinases, whose activity is inhibited by the agents of Formula I, are involved.

Such disorders may include those of neuronal, glial, astrocytal, hypothalamic, and other glandular, macrophagal, epithelial, stromal, and blastocoelic nature in which aberrant function, expression, activation or signalling of the erbB tyrosine kinases may be involved. In addition, compounds of Formula I may have therapeutic utility in inflammatory, angiogenic and immunologic disorders involving both identified and as yet unidentified tyrosine kinases which are inhibited by compounds of Formula I.

The in vitro activity of the active compounds in inhibiting the receptor tyrosine kinase (and thus subsequent proliferative response, e.g., cancer) may be determined by the procedure detailed below.

Activity of the active compunds, in vitro, can be determined by the amount of inhibition of the phosphorylation of an exogenous substrate (e.g., Lys$_3$-Gastrin or polyGluTyr (4:1) random copolymer (I. Posner et. al., J. Biol. Chem. 267 (29), 20638–47 (1992)) on tyrosine by epidermal growth factor receptor kinase by a test compound relative to a control. Affinity purified, soluble human EGF receptor (96 ng) is obtained according to the procedure in G. N. Gill, W. Weber, Methods in Enzymology 146, 82–88 (1987) from A431 cells (American Type Culture Collection, Rockville, Md.) and preincubated in a microfuge tube with EGF (2 μg/ml) in phosphorylation buffer+vanadate (PBV: 50 mM HEPES, pH 7.4; 125 mM NaCl; 24 mM MgCl$_2$; 100 μM sodium orthovanadate), in a total volume of 10 μl, for 20–30 minutes at room temperature. The test compound, dissolved in dimethylsulfoxide (DMSO), is diluted in PBV, and 10 μl is mixed with the EGF receptor /EGF mix, and incubated for 10–30 minutes at 30° C. The phosphorylation reaction is initiated by addition of 20 μl $^{33}$P-ATP/substrate mix (120 μM Lys$_3$-Gastrin (sequence in single letter code for amino acids, KKKGPWLEEEEEAYGWLDF), 50 mM Hepes pH 7.4, 40 μM ATP, 2 μCi γ-[$^{33}$P]-ATP) to the EGFr/EGF mix and incubated for 20 minutes at room temperature. The reaction is stopped by addition of 10 μl stop solution (0.5M EDTA, pH 8; 2mM ATP) and 6 μl 2N HCl. The tubes are centrifuged at 14,000 RPM, 4° C., for 10 minutes. 35 μl of supernatant from each tube is pipetted onto a 2.5 cm circle of Whatman P81 paper, bulk washed four times in 5% acetic acid, 1 liter per wash, and then air dried. This results in the binding of substrate to the paper with loss of free ATP on washing. The [$^{33}$P] incorporated is measured by liquid scintillation counting. Incorporation in the absence of substrate (e.g., lys$_3$-gastrin) is subtracted from all values as a background and percent inhibition is calculated relative to controls without test compound present.

Such assays, carried out with a range of doses of test compounds, allow the determination of an approximate $IC_{50}$ value for the in vitro inhibition of EGFR kinase activity. Although the inhibitory properties of the compounds of Formula I vary with structural change as expected, the activity generally exhibited by these agents, determined in the manner described above, is in the range of $IC_{50}$= 0.0001–30 µM.

Activity of the active compounds, in vivo, can be determined by the amount of inhibition of tumor growth by a test compound relative to a control. The tumor growth inhibitory effects of various compounds are measured according to the methods of Corbett T. H., et al. "Tumor Induction Relationships in Development of Transplantable Cancers of the Colon in Mice for Chemotherapy Assays, with a Note on Carcinogen Structure", *Cancer Res.*, 35, 2434–2439 (1975) and Corbett, T. H., et al., "A Mouse Colon-tumor Model for Experimental Therapy", *Cancer Chemother. Rep. (Part 2)*, 5, 169–186 (1975), with slight modifications. Tumors are induced in the left flank by s.c. injection of $1\times10^6$ log phase cultured tumor cells (human MDA-MB-468 breast or human HN5 head and neck carcinoma cells) suspended in 0.10 ml RPMI 1640. After sufficient time has elapsed for the tumors to become palpable (2–3 mm in diameter) the test animals (athymic mice) are treated with active compound (formulated by dissolution in DMSO typically at a concentration of 50 to 100 mg/mL followed by 1:9 dilution into saline or, alternatively, 1:9 dilution into 0.1% Pluronic® P105 in 0.9% saline) by the intraperitoneal (ip) or oral (po) routes of administration twice daily (i.e., every 12 hours) for 5 consecutive days. In order to determine an anti-tumor effect, the tumor is measured in millimeters with Vernier calipers across two diameters and the tumor size (mg) is calculated using the formula: Tumor weight=(length× [width]$^2$)/2, according to the methods of Geran, R. I., et al. "Protocols for Screening Chemical Agents and Natural Products Against Animal Tumors and Other Biological Systems", Third Edition, *Cancer Chemother. Rep.*, 3, 1–104 (1972). Results are expressed as percent inhibition, according to the formula: Inhibition (%)=(TuW$_{control}$–TuW$_{test}$)/ TuW$_{control}$×100%. The flank site of tumor implantation provides reproducible dose/response effects for a variety of chemotherapeutic agents, and the method of measurement (tumor diameter) is a reliable method for assessing tumor growth rates.

Administration of the active compounds can be effected by any method which enables delivery of the compounds to the site of action (e.g., cancer cells). These methods include oral routes, intraduodenal routes, parenteral injection (including intravenous, subcutaneous, intramuscular, intravascular or infusion), topical administration, etc.

The amount of active compound administered will, of course, be dependent on the subject being treated, on the severity of the affliction, on the manner of administration and on the judgement of the prescribing physician. However, an effective dosage is in the range of approximately 0.001–100 mg/kg, preferably 1 to 35 mg/kg in single or divided doses. For an average 70 kg human, this would amount to 0.05 to 7 g/day, preferably 0.2 to 2.5 g/day.

The composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Pharmaceutical compositions according to the invention may contain 0.1%–95% of the compound, preferably 1%–70%. In any event, the composition or formulation to be administered will contain a quantity of active compound in an amount effective to alleviate or reduce the signs in the subject being treated, i.e., hyperproliferative diseases, over the course of the treatment.

Exemplary parenteral administration forms include solutions or suspensions of active compounds in sterile aqueous solutions, for example aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences., Mack Publishing Company, Easter, Pa., 15th Edition (1975).

The hyperproliferative disease treatment described above may be applied as a sole therapy or may involve, in addition to the active compound, one or more other antitumor substances. Such conjoint treatment may be achieved by way of the simultaneous, sequential, cyclic or separate dosing of the individual components of the treatment.

High pressure liquid chromatography (HPLC) used in the following examples and preparations was effected according to the following method unless modified in specific examples. Perkin-Elmer Pecosphere® 3×3C cartridge column (3mm×3cm, C18; available from Perkin Elmer Corp., Norwalk, Conn. 06859) with a Brownlee (trademark) RP-8Newguard precolumn (7 micron, 3.2 mm×15 mm, available from Applied Biosystems Inc. San Jose, Calif. 95134) which was previously equilibrated in pH 4.50, 200 mM ammonium acetate buffer. Samples were eluted using a linear gradient of 0–100% acetonitrile/pH4.50, 200 mM NH$_4$ acetate over 10 minutes with a flow rate of 3.0 mL/min. Chromatograms were generated over the range 240–400 nm using a diode array detector.

It should be understood that the invention is not limited to the particular embodiments shown and described herein, but that various changes and modifications may be made without departing from the spirit and scope of the invention as defined by the claims.

EXAMPLE 1

(4-Azidophenyl)-(6,7-dimethoxyquinazolin-4-yl)-amine Hydrochloride

4-Chloro-6,7-dimethoxyquinazoline (250 mg, 1.12 mmol) and 4-azidoaniline hydrochloride (200 mg, 1.11 mmol) were refluxed in 10 mL of isopropyl alcohol for 0.5 hour, cooled and filtered to afford solid title product which was washed with 10 mL of isopropyl alcohol and dried in vacuo, at 70° C., 392 mg (98%); mp 200°–205° C. (dec).

EXAMPLE 2

(6,7-Dimethoxyquinazolin-4-yl)-(3-ethynylphenyl)-amine Hydrochloride

4-Chloro-6,7-dimethoxyquinazoline (250 mg, 1.12 mmol) and 3-ethynyl-aniline (137 mg, 1.17 mmol) were refluxed in 10 mL of isopropyl alcohol for 0.5 hour, cooled and filtered to afford solid title product which was washed with 10 mL of isopropyl alcohol and dried in vacuo, at 70° C., 338 mg (99%); mp 269°–270° C.

EXAMPLE 3

(6,7-Dimethoxyquinazolin-4-yl)-[3-(3'-hydroxypropyn-1-yl)phenyl]-amine

A mixture of (3'-bromophenyl)-(6,7-dimethoxyquinazolin-4-yl)-amine hydrochloride (250 mg, 0.591 mmol), tetrakis(triphenylphosphine)palladium (100 mg), propargyl alcohol (600 µL), 7 mL of dry, nitrogen purged diethylamine and cuprous iodide (10 mg) was refluxed for 5 hours, cooled and filtered to afford solid title product which was washed two times with 2 mL of 50% diethylamine:methanol; 136 mg. The solid was recrystallized from methanol to give pure title product after drying, in vacuo., at 70° C., 73 mg (37%); mp 267°–268° C.

EXAMPLE 4

[(3-(2'-Aminomethyl-ethynyl)phenyl]-(6,7-dimethoxyquinazolin-4-yl)-amine Hydrochloride The title product of Example 3 (50 mg, 0.149 mmol), triphenylphosphine (60 mg, 0.225 mmol)), phthalimide (165 mg, 1.12 mmol) and diethyl azodicarboxylate (36 µL, 0.228 mmol) were stirred at room temperature in 3 mL of dry tetrahydrofuran for 16 hours. The reaction mixture was concentrated to a solid and flash chromatographed on silica gel eluted with 15% acetone:methylene chloride to afford pure solid [3-(2'-{phthalimidomethyl}-ethynyl)phenyl]-(6, 7-dimethoxyquinazoline-4-yl)amine which was converted to its hydrochloride salt by addition of 1 mL of anhydrous 1M HCl in methanol followed by 3 mL of isopropyl alcohol. The salt was collected by filtration, dried and used immediately in the next step; 15 mg. This 15 mg, 0.0323 mmol was treated with 0.5 ml of hydrazine hydrate and 1 mL of methanol for 0.5 hours. The reaction mixture was evaporated, in vacuo, and the product isolated by flash chromatography eluted with 10% methanol in methylene chloride. Pure title product was isolated after conversion to its hydrochloride salt with 1 mL of 1M HCl in methanol, precipitation with isopropyl alcohol and diethyl ether and drying, in vacuo.; 5.6 mg (47%) mp 275° C. dec.

EXAMPLE 5

(3-Ethynylphenyl)-(6-nitroquinazolin-4-yl)-amine Hydrochloride

4-Chloro-6-nitroquinazoline (1.06 g,5.00 mmol) and 3-ethynylaniline (1.00 g,5.30 mmol) were refluxed in 10 mL of isopropyl alcohol for 3 hours, cooled and, after 16 hours at room temperature, filtered to afford solid title product which was washed with 10 mL of isopropyl alcohol and dried in vacuo, at 70° C., 1.27 g (78%); mp 255°–256° C.

EXAMPLE 6

(6,7-Dimethoxyquinazolin-4-yl)-(4-ethynylphenyl)-amine

The title product was prepared in the following three step sequence without purification of the intermediates. 4-Chloro-6,7-dimethoxyquinazoline (250 mg, 1.113 mmol) and 4-iodoaniline (268 mg, 1.224 mmol) were refluxed in 10 mL of isopropyl alcohol for 3 hours, cooled to room temperature and filtered to afford solid (4-iodophenyl)-(6,7-dimethoxyquinazoline-4-yl)amine hydrochloride which was washed with 10 mL of isopropyl alcohol and dried in vacuo at 70° C., 396 mg (76%). A mixture consisting of (4'-iodophenyl)-(6,7-dimethoxyquinazoline-4-yl)amine hydrochloride (250 mg, 0.564 mmol), tetrakis (triphenylphosphine)palladium (50 mg), trimethylsilylacetylene (160 µL, 1.13 mmol), 4 mL of dry, nitrogen purged diethylamine and cuprous iodide (10 mg) was refluxed for 2 hours, cooled and concentrated in vacuo, to afford a residue which was partitioned between chloroform and 1N HCL. Solid [4-(2'-{trimethylsilyl}-ethynyl) phenyl]-(6,7-dimethoxyquinazoline-4-yl)amine formed at the interface of the two liquid phases and was filtered and dried in vacuo; 170 mg (80%).

[4-(2'-{Trimethylsilyl}ethynyl)phenyl]-(6,7-dimethoxyquinazoline-4-yl)amine (100 mg, 0.265 mmol) and anhydrous potassium carbonate (125 mg, 0.906 mmol) were stirred in 3 mL of methanol and 1 mL of water at room temperature for 2.5 hours. The reaction mixture was concentrated in vacuo, and partitioned between 20 mL of chloroform and 20 mL of 1N hydrochloric acid. The organic layer was dried with magnesium sulfate, filtered and vacuum evaporated to give the title product which was triturated with diethyl ether and dried in vacuo at 70° C.; 81 mg (90%) mp 239° C. dec.

EXAMPLE 7

(6,7-Dimethoxyquinazolin-4-yl)-(3-ethynyl-2-methylphenyl)-amine

The title product was prepared in the following three step sequence with out purification of the intermediates. A mixture consisting of 3-bromo-2-methylaniline (1.00 g, 5.37 mmol), tetrakis(triphenylphosphine)palladium (200 mg), trimethylsilylacetylene (1.053 g, 10.75 mmol), 10 mL of dry, nitrogen purged diethylamine and cuprous iodide 910 mg) was refluxed for 16 hours, cooled and concentrated, in vacuo, to afford a residue which was partitioned between chloroform and 1N HCL. The organic layer was washed with brine, dried with magnesium sulfate and vacuum evaporated to yield a residue, 3-[2'-(trimethylsilyl)ethynyl] -2-methylaniline which was purified by flash chromatography on silica gel eluted with 1:1 hexanes:methylene chloride; 200 mg (18%).

4-Chloro-6,7-dimethoxyquinazoline (104 mg, 0.466 mmol) and 3-[2'-(trimethylsilyl)ethinyl]-2-methylaniline (100 mg, 0.491 mmol) were refluxed in 3 mL of isopropyl alcohol for 16 hour, cooled to room temperature and filtered to afford a residue of solid {3-[2'-(trimethylsilyl)ethynyl]-2'-methylphenyl]}-(6,7dimethoxyquinazoline-4-yl)amine hydrochloride which was washed with 10 mL of isopropyl alcohol and triturated for 16 hours with diethyl ether. Thin layer chromatography on silica gel eluted with 9:1 chloroform:methanol indicated that the residue was impure product. The residue was purified by flash chromatography on silica gel eluted with 9:1 methylene chloride:methanol to afford after concentration and drying, in vacuo, pure product, 64 mg (33%). The product was dissolved in 3 mL of methanol and treated with 64 mg of anhydrous potassium carbonate at room temperature for 3 hours. The reaction mixture was concentrated in vacuo and partitioned between 1N HCl and chloroform. Solid title product formed at the interface of the two liquid phases and was filtered and dried, in vacuo; 40 mg (84%) mp 225° C. dec.

EXAMPLE 8

(6-Amino-quinazolin-4-yl)-(3-ethynylphenyl)-amine (3-Ethynyl-phenyl)-(6-nitro-quinazolin-4-yl)-amine hydrochloride (500 mg, 1.50 mmol) was dissolved in 10 mL of formic acid and treated portion-wise with sodium dithionite (1.10 g, 6.28 mmol) at room temperature. After 2 hours the mixture was quenched with 120 mL of water and filtered. The filtrate was evaporated in vacuo to a residue which was dissolved in 100 mL of 1:1 methanol:chloroform, filtered and evaporated in vacuo to a second residue. This was triturated with 200 mL of 5% sodium bicarbonate for 30 minutes, filtered, washed with water and dried in vacuo for 16 hours. Flash chromatography on silica gel eluted with ethyl acetate afforded pure (6-aminoquinazolin-4-yl)-(3-ethynylphenyl)-amine; 140 mg (34%); mp 165° C. dec.

EXAMPLE 9

(3-Ethynylphenyl)-(6-methanesulfonylaminoquinazolin-4-yl}-amine

The title product of Example 8 (100 mg, 0.384 mmol), pyridine (140 µL, 1.68 mmol) and methanesulfonyl chloride (99 µL, 1.26 mmol) were refluxed in 10 mL of 1,2-dichloroethane for 7 hours. The reaction mixture was cooled and evaporated in a vacuo to a residue which was triturated in 10 mL of 1N HCl, filtered and dried in vacuo to yield (3-ethynylphenyl)-(6-methanesulfonylaminoquinazoline-4-yl)amine; 102 mg (78%) mp 248° C. dec.

EXAMPLE 10

(3-Ethynylphenyl)-(6,7-methylenedioxyquinazolin-4-yl)-amine Hydrochloride

4-Chloro-6,7-methylenedioxyquinazoline (200 mg, 1.04 mmol) and 3-ethynylaniline (127 mg, 1.09 mmol) were refluxed in 5 mL of isopropyl alcohol for 16 hour, cooled and filtered to afford solid title product which was washed with 10 mL of isopropyl alcohol and dried in vacuo at 70° C., 266 mg (79%); mp >350° C.

EXAMPLE 11

((6,7-Dimethoxyquinazolin-4-yl)-3-ethynyl-6-methylphenyl)-amine Hydrochloride

The title product was prepared in the following three step sequence without purification of the intermediates. A mixture consisting of 4-bromo-2-nitrotoluene (1.50 g, 6.94 mmol) tetrakis(triphenylphosphine)palladium (750 mg), trimethylsilylacetylene (3.00 mL, 21.21 mmol) and cuprous iodide (20 mg) in 20 mL of nitrogen purged, dry diethylamine was refluxed for 2 hours, cooled and concentrated, in vacuo, to afford a residue which was partitioned between 100 mL of ethyl acetate and 100 mL of 1N HCl. The organic layer was washed two times with 50 mL of 1N HCl followed by brine, dried with magnesium sulfate and vacuum evaporated to a residue. The residue was dissolved in 10 mL of ethyl acetate and diluted with 200 mL of petroleum ether. The solids were filtered off and the oil, obtained upon vacuum evaporation of the filtrate, solidified to give 4-[2'-(trimethylsilyl)ethinyl]-2-nitrotoluene. This product was reduced to the amino product by treatment with iron powder (1.76 g, 98.5 mmol) in 30 mL of methanol and 5 mL of concentrated hydrochloric acid at 80° C. for 2 hours. The cooled reaction mixture was filtered through Celite® and the filtrate was evaporated in vacuum. The residue was partitioned between ethyl acetate and 5% aqueous sodium bicarbonate. The organic layer was washed with brine, dried with magnesium sulfate, filtered and vacuum evaporated to yield an oil, 5-[2'-(trimethylsilyl)ethynyl]-2-methylaniline which solidified upon standing: 1.37 g.

The above product (185 mg, 0.909 mmol) and 4-chloro-6,7-dimethoxyquinazoline (200 mg, 0.890 mmol) were refluxed in tert-butyl alcohol for 16 hours. After cooling the reaction mixture was filtered to yield pure |2-methyl-5-(2'-{trimethylsilyl}-ethynyl)-phenyl]-(6,7-dimethoxyquinazoline-4-yl-amine hydrochloride after washing with ether and drying in vacuum; 326 mg (85%). The trimethylsilyl group was removed by dissolving the above product in 5 mL of methanol and 1 mL of water and treatment with potassium carbonate (320 mg). After stirring for 1 hour the mixture was filtered and concentrated in vacuo. The residue thus obtained was partitioned between 100 mL of methylene chloride and 100 mL of 1N HCl. The aqueous layer was extracted with an additional 100 mL of methylene chloride. The pooled organic layers were dried with magnesium sulfate, filtered and vacuum evaporated to a residue which was dissolved in anhydrous 1N HCl in methanol, concentrated and precipitated with ether. The solid title product was collected by filtration and washed with diethyl ether then dried in vacuo at 70° C.; 236 mg (88%) mp 266°-267° C.

EXAMPLE 12

(3-Ethynylphenyl)-(7-nitroquinazolin-4-yl)-amine Hydrochloride

4-Chloro-7-nitroquinazoline (7.97 g, 38.0 mmol) and 3-ethynylaniline (4.54 g, 38.8 mmol) were refluxed in 125 mL of tert-butyl alcohol for 3 hours, cooled to room temperature and filtered to afford the title product as a solid which was washed with 10 mL of isopropyl alcohol and dried in vacuo at 70° C., 9.95 g (80%); mp 209°-210° C. dec.

EXAMPLE 13

(3-Ethynylphenyl)-|6-(4'-toluenesulfonylamino)-quinazolin-4-yl]-amine Hydrochloride The title product of example 8 (0.201 mg, 0.774 mmol) and 4-toluenesulfonyl chloride (0.441 mg, 2.31 mmol) were refluxed in 3 mL of 1,2-dichloroethane and 0.5 mL of pyridine for 5 minutes. The reaction mixture was cooled to room temperature, diluted with 75 mL of ethyl acetate and washed two times with 75 mL of water once with 75 mL of 3% sodium bicarbonate and once with 75 mL of brine. The organic layer was dried with magnesium sulfate, filtered and vacuum evaporated to a residue which was purified by chromatography using a Chromatotron (trademark) eluted with ethyl acetate, to afford solid title product; 86.7 mg (27%) mp 220°–222° C.

EXAMPLE 14

(3-Ethynylphenyl)-{6-[2'-phthalimido-ethan-1'-ylsulfonylamino]quinazolin-4-yl}-amine Hydrochloride The title product of example 8 (0.20 mg, 0.768 mmol) and 2-phthalimido-1-ethanesulfonyl chloride (0.615 mg, 2.25 mmol) were refluxed in 2 mL of 1,2-dichloroethane and 0.5 mL of pyridine for 16 hours, cooled to room temperature, diluted with 100 mL of chloroform and washed with 50 mL of 3% sodium bicarbonate and 50 mL of brine. The organic layer was dried with magnesium sulfate, filtered and vacuum evaporated to a residue which was dissolved in minimal methylene chloride and precipitated with petroleum ether, 188 mg. The precipitate was purified by chromatography using Chromatotron@ eluted with ethyl acetate, to afford the title product as a solid; 53.4 mg (14%) mp 197°–200° C.

EXAMPLE 15

(3-Ethynylphenyl)-(6-guanidinoquinazolin-4-yl)-amine Hydrochloride

The title product of example 8, (0.302 mg, 1.16 mmol) and 3,5-dimethylpyrazole-1-carboxamidine (0.328 mg, 2.36 mmol) were refluxed in 10 mL of 1,2-dichloroethane and 0.97 mL of acetic acid for 24 hours, cooled to room temperature and filtered to yield the crude acetate of the title product. The product was dissolved in 35 mL of methanol and treated with 15 mL of anhydrous 1N HCl in methanol for 15 minutes and then precipitated with 75 mL of diethyl ether. Solid title product was collected by filtration and dried in vacuo at 70° C.; 91.2 mg (23%) mp>400° C.

EXAMPLE 16

(7-Aminoquinazolin-4-yl)-(3-ethynylphenyl)-amine

The title product of example 12 (1.039 g, 3.18 mmol) was dissolved in 50 mL of tetrahydrofuran, 10 mL of methanol and 5 mL of chloroform at 50° C. Sodium dihydrogen phosphite (NaH$_2$PO$_2$, 3.822 g, 36 mmol) and 10% palladium on carbon (0.19 g) were added followed by dropwise addition of 10 mL of water. When 3 mL of water had been added the mixture became noticeably more homogeneous. After 1 hour the mixture was filtered through Celite. The Celite was washed thoroughly with methanol and chloroform. The combined organic solutions were vacuum evaporated to a residue which was triturated with water, 3% aqueous sodium bicarbonate and filtered. The solid title product was washed with water then diethyl ether and dried in vacuo, 1.054 gm (127%, wet). A portion of the above product was recrystallized from a minimum amount of hot ethanol and water to give, after removal of a small first crop of impure material, pure title product, (43%), mp 180° C. (dec).

EXAMPLE 17

(3-Ethynylphenyl)-(7-methoxyquinazolin-4-yl)-amine Hydrochloride

4-Chloro-7-methoxyquinazoline (274 mg, 3.72 mmol) and 3-ethynylaniline (436 mg, 3.72 mmol) were refluxed in 15 mL of tert-butyl alcohol for 3 hours, cooled and filtered to afford solid title product which was washed with 10 mL of isopropyl alcohol and dried in vacuo at 70° C., 977 mg (84%); mp 229°–231° C.

EXAMPLE 18

(6-Carbomethoxyquinazolin-4-yl)-(3-ethynylphenyl)-amine Hydrochloride

4-Chloro-6-carbomethoxyquinazoline (100 mg, 0.450 mmol) and 3-ethynylaniline hydrochloride (53.4 mg, 0.456 mmol) were refluxed in 2 mL of tert-butyl alcohol for 2 hours, cooled, diluted with 2 mL of isopropyl alcohol and filtered to afford solid title product which was washed with 10 mL of diethyl ether and dried, in vacuo, at 70° C., 122 mg (80%); mp 232°–233° C. (dec).

EXAMPLE 19

(7-Carbomethoxyquinazolin-4-yl)-(3-ethynylphenyl)-amine Hydrochloride

4-Chloro-7-carbomethoxyquinazoline (202 mg, 0.907 mmol) and 3-ethynylaniline (110 mg, 0.939 mmol) were refluxed in 4 mL of tert-butyl alcohol for 2 hours, cooled, diluted with 4 mL of isopropyl alcohol and filtered to afford solid title product which was washed with 10 mL of diethyl ether and dried, in vacuo, at 70° C., 248 mg (80%); mp 219.5°–221° C.

EXAMPLE 20

[6-,7-Bis-(2-methoxyethoxy)-quinazolin-4-yl]-(3-ethynylphenyl)amine Hydrochloride 3-Ethynylaniline (37 mg, 0.32 mmol.), and 4-chloro-6,7-bis-(2-methoxy-ethoxy)quinazoline (90 mg, 0.29 mmol) were added to isopropanol (1.5 mL) containing pyridine (25 μL, 0.32 mmol) and the mixture was refluxed 4 hours under an atomospher of dry nitrogen. The solvent was removed, in vacuo, and the residue partitioned between 10% methanol in CHCl$_3$ and saturated aqueous NaHCO$_3$. The organic phase was dried over Na$_2$SO$_4$, filtered and concentrated in vacuo. The residue was flash chromatographed on silica using 30% acetone in hexanes to afford 81 mg of the free base of the title product as a pale yellow solid. The free-base was dissolved in a minimum volume of CHCl$_3$, diluted with several volumes of ether, and titrated with 1M HCl in ether to precipitate the title product as its hydrochloride salt; 90 mg; 71%; mp 228°–230° C.

EXAMPLE 21

(3-Azidophenyl)-(6,7-dimethoxyquinazolin-4-yl) amine

4-Chloro-6,7-dimethoxyquinazoline (5.01 g, 22.3 mmol) was added in portions, over 1.5 hours, to m-phenylenediamine (2.66 g, 24.6 mmol) in refluxing isopropanol (100 mL) under an atmosphere of dry nitrogen. After the addition was complete the mixture was heated at reflux for 4 hours. The mixture was cooled to 20° C., and the precipitate was filtered, washed with chilled isopropanol and dried in vacuo to afford 6.97 g (93%) of (3-aminophenyl)-(6,7-dimethoxyquinazolin-4-yl)amine hydrochloride (LC-MS: 297 (MH$^+$). To a solution of the above product (50 mg, 0.169 mmol) in 80% acetic acid/H$_2$O (2 mL), at 0° C., was added a solution of NaNO$_2$ (18.4 mg, 0.186 mmol) in H$_2$O (100 μL). After stirring 10 minutes at 0° C. a solution of NaN$_3$ (12 mg, 0.185 mmol) in H$_2$O (100 µL) was added. The mixture was allowed to warm to 20° C. and stirred for 1.5 hours. The reaction mixture was lyophilized and the residue partitioned between ethyl acetate and saturated aqueous NaHCO$_3$. The organic phase was wahsed further with brine, dried over Na$_2$SO$_4$, filtered, and concentrated, in vacuo. Recrystallization from CHCl$_3$/hexanes afforded 36 mg of the title product as a white solid; mp 110°–113° C.

EXAMPLE 22

(3-Azido-5-chlorophenyl)-(6,7-dimethoxyquinazolin-4-yl)amine

4-Chloro-6,7-dimethoxyquinazoline (200 mg, 0.89 mmol) and 5-amino-3-chloroaniline (253 mg, 1.78 mmol) were combined in isopropanol (3 mL) and heated to reflux for 16 hours under an atmosphere of dry nitrogen. After cooling to 20° C. the mixture was diluted with methanol (5 mL) and the resulting precipitate was filtered and dried, in vacuo, to afford 252 mg (77%) of (3-amino-5-chlorophenyl)-(6,7-dimethoxyquinazolin-4-yl)amine hydrochloride (mp. 298°–301° C.; LC-MS: 331 (MH+)). A portion of this product (175 mg, 0.476 mmol) was dissolved in 80% acetic acid/H$_2$O (12 mL), cooled to 0° C., and a solution of NaNO$_2$ (36 mg, 0.516 mmol) in H$_2$O (300 µL) was added. The solution was stirred for 10 minutes at 0° C. and NaN$_3$ (33 mg, 0.50 mmol) in H$_2$O (300 µL) was added. The reaction mixture was allowed to warm to 20° C. and stirred 16 hours. The resulting precipitate was filtered and dissolved in 10% methanol in CHCl$_3$ and the solution was washed with saturated aqueous NaHCO$_3$, and brine, dried over Na$_2$SO$_4$, filtered and concentrated in vacuo to yield 59 mg (35%) of the title product as a yellow solid; mp 205°–206° C.

EXAMPLE 23

(3-Ethynylphenyl)-(6-methanesulfonyl-quinazolin-4-yl-amine Hydrochloride

6-Methanesulfonyl-quinazolin-4-one (200 mg, 0.89 mmol), triphenyl phosphine (566 mg, 2.15 mmol) and carbon tetrachloride (815 µL, 8.92 mmol) were refluxed in 3 mL of chloroform for 3.5 hours. The solvent was vacuum evaporated to afford a residue. This was dissolved in 5 mL of isopropyl alcohol and 3-ethynylaniline (156 mg, 1.33 mmol) and heated at reflux for 16 hours. The cooled reaction mixture was filtered, washed with a minimum of cold isopropyl alcohol and dried in vacuo at 70° C. for 16 hours to afford pure title product; 63 mg (20%) mp 281°–282° C.

EXAMPLE 24

(6-Ethansulfanyl-quinazolin-4-yl)-(3-ethynylphenyl)-amine Hydrochloride

6-Ethanesulfanyl-quinazolin-4-one (100 mg, 0.48 mmol), triphenyl phosphine (305 mg, 1.16 mmol) and 3 mL of carbon tetrachloride were refluxed for 16 hours. The solvent was vacuum evaporated to afford a residue. This was dissolved in 5 mL of isopropyl alcohol and 3-ethynylaniline (68 mg, 0.58 mmol) and heated at reflux for 1 hour. The cooled reaction mixture was filtered, washed with a minimum of cold isopropyl alcohol and dried in vacuo at 70° C. for 16 hours to afford pure title product; 70 mg (42%) mp 239°–40° C.

EXAMPLE 25

(6,7-Dimethoxy-quinazolin-4-yl)-(3-ethynyl-4-fluoro-phenyl)-amine Hydrochloride

4-Chloro-6,7-dimethoxyquinazoline (500 mg, 2.23 mmol) and 3-(2'-trimethylsilylethynyl)-4-fluoroaniline (507 mg, 2.44 mmol) were refluxed in 5 mL of tert-butyl alcohol for 16 hours, cooled and filtered to afford solid (6,7-dimethoxy-quinazolin-4-yl)-(3'-ethynyl-phenyl)-amine hydrochloride which was washed with 10 mL of isopropyl alcohol and dried in vacuo at 70° C., 832 mg (83%). This was reacted in 10 mL of methanol and 1 drop of water containing 250 mg of potassium carbonate for 3 hours. The mixture was filtered and the filtrate vacuum evaoprated. This residue was triturated for 1 hour with 1N hydrochloric acid, filtered and washed with a minimum amount of water then methanol and dried in vacuo; 506 mg (63%) mp 229° C. dec.

3-(2'-Trimethylsilyl-ethynyl)-4-fluoroaniline, used above, was prepared from 3-bromo-4-fluoroaniline (7.0 gm, 36.8 mmol) tetrakis(triphenylphosphine)palladium (1.4 gm), trimethylsilyl-acetylene (7.2 gm, 74 mmol) and cuprous iodide (40 mg) in 140 mL of nitrogen purged dry diethylamine at reflux for 16 hours. The cooled reaction mixture was filtered through Celite and the Celite washed with ether. The combined filtrates were vacuum evaporated to a residue which was purified by flash chromatography on silica gel eluted with 35% hexanes in methylene chloride. Fractions containing the pure 3-(2'-trimethylsilyl-ethynyl)-4-fluoroaniline were vacuum evaporated to a residue and used without further purification.

EXAMPLE 26

(6,7-Dimethoxy-quinazolin-4-yl)-(3-propyn-1-yl) phenyl)-amine Hydrochloride

4-Chloro-6,7-dimethoxyquinazoline (585 mg, 2.60 mmol) and 3-(propyn-1-yl)aniline (361 mg, 2.74 mmol) were refluxed in 5 mL of tert-butyl alcohol for 16 hours, cooled and filtered to afford solid (6,7-dimethoxy-quinazolin-4-yl)-[3-(propyn-1-yl)phenyl)]-amine hydrochloride which was washed with 5 mL of isopropyl alcohol and 25 mL of ether then dried in vacuo at 70° C., 869 mg (94%); mp 260°–261° C.

3-(Propyn-1-yl)aniline, used above, was prepared from 3-bromo-nitrobenzene in four steps. 3-Bromo-nitrobenzene (5.0 gm, 24.7 mmol), tetrakis(triphenylphosphine)palladium (1.0 gm), trimethylsilyl-acetylene (3.6 gm, 37 mmol) and cuprous iodide (20 mg) in 20 mL of nitrogen purged, dry diethylamine at reflux for 16 hours. The cooled reaction mixture was vacuum evaporated, diluted with 50 mL of methylene chloride and 50 mL of 1N hydrochloric acid and filtered. The organic layer was collected and dried with magnesium sulfate filtered and vacuum evaporated to a residue. The 3-trimethylsilylethynylnitrobenzene was purified by flash chromatography on silica gel eluted with 2:1 hexanes:methylene chloride. Fractions containing the pure material were vacuum evaporated to afford pure 3-trimethylsilylethynyl nitrobenzene (4.6 gm). 4.0 gm of this were dissolved in 30 mL of methanol and 1 drop of water containing 1.16 gm of potassium carbonate. After one hour the mixture was vacuum evaporated and diluted with 100 mL of methylene chloride. The organic layer was washed with 100 mL of 1N hydrochloric acid, dried with magnesium sulfate, filtered and vacuum evaporated to a residue (2.96 gm). 790 mg of this was dissolved in 10 mL of benzene and treated with finely pulverized 87% potassium hydroxide (377 mg, 5.91 mmol), methyl iodide (2 mL) and 10 mg of 18-Crown-6 (Aldrich) at reflux for 16 hours. An additional 0.5 mL of methyl iodide were added and the reflux continued for an additional 2 hours. The cooled reaction mixture was vacuum evaporated to a residue which was diluted with 100 mL of methylene chloride and washed with 100 mL of 1N hydrochloric acid, dried with magnesium sulfate, filtered and vacuum evaporated to an oil. This was purified by flash chromatography on silica gel eluted with 1:1 hexanes:methylene chloride. Fractions containing pure 3-(propyn-1-yl)-nitrobenzene were vacuum evaporated to an oil which was used without further purification; 530 mg (61%). 3-(Propyn-1-yl)-nitrobenzene (530 mg, 3.3 mmol), iron powder (400 mg, 7.27 mmol), 3 mL of concentrated hydrochloric acid and 10 mL of methanol were refluxed for 1 hour. The reaction mixture was filtered and vacuum evaporated to a solid which was partitioned between 100 mL of methylene chloride and 100 mL of 1N sodium hydroxide. The two phases were filtered and then the organic phase was separated, dried with magnesium sulfate, filtered and vacuum evaporated to an oil which was used directly in the preparation of the title product; 321 mg (78%).

EXAMPLE 27

[6,7-Bis-(2-methoxy-ethoxy)-quinazolin-4-yl]-(3-ethynyl-4-fluoro-phenyl)-amine Hydrochloride 4-Chloro-6,7-bis-(2-methoxy-ethoxy)-quinazoline (140 mg, 0.446 mmol) and 3-ethynyl-4-fluoroaniline (66 mg, 0.452 mmol) were reacted in refluxing isopropanol (3 mL) under an atmosphere of $N_2$ for 16 hours. The solvent was removed in vacuo and the residue was partitioned between $CHCl_3$ and saturated aqueous $NaHCO_3$. The organic extracts were washed with brine, dried over $Na_2SO_4$, filtered and concentrated in vacuo. The crude product was chromatographed on silica using 40% acetone/$CH_2Cl_2$ to provide 116 mg of the pure title product as its free base. This oil was dissolved in a minimum volume of $CHCl_3$, diluted with several volumes of ether and titrated with 1M HCl in ether to precipitate the title product as a white solid (99 mg; 50%; M.P. 170°–190° C. (dec); LC-MS: 412 ($MH^+$); anal. RP18-HPLC RT: 4.33 min.).

EXAMPLE 28

[6,7-Bis-(2-methoxy-ethoxy)-quinazolin-4-yl]-(5-ethynyl-2-methyl-phenyl)-amine Hydrochloride 4-Chloro-6,7-bis-(2-methoxy-ethoxy)-quinazoline (153 mg, 0.49 mmol), pyridine (40 μL) and 3-ethynyl-6-methylaniline (71 mg, 0.54 mmol) were reacted in DMF (3 mL) at 110° C. under an atmosphere of $N_2$ for 36 hours. The solvent was removed in vacuo and the residue was partitioned between $CHCl_3$ and saturated aqueous $NaHCO_3$. The organic extracts were washed with brine, dried over $Na_2SO_4$, filtered and concentrated in vacuo. The crude product was chromatographed on silica using 40% acetone/$CH_2Cl_2$ to provide 40 mg (19%) of pure product as its free base. This oil was dissolved in a minimum volume of $CHCl_3$, diluted with several volumes of ether, and triturated with 1M HCl in ether to precipitate the title product as a white solid (M.P. 170°–185° C. (dec); LC-MS: 408 ($MH^+$); anal. RP18-HPLC RT: 3.93 min.).

EXAMPLE 29

[6,7-Bis-(2-chloro-ethoxy)-quinazolin-4-yl]-(3-ethynyl-phenyl)-amine Hydrochloride 4-Chloro-6,7-bis-(2-chloro-ethoxy)-quinazoline (600 mg, 1.87 mmol) and 3-ethynyl-aniline (219 mg, 1.87 mmol) were reacted in refluxing isopropanol (15 mL) under an atmosphere of $N_2$ for 2.5 hours. The mixture was cooled to 20° C. and the precipitated product was filtered, washed With isopropanol and ether and dried in vacuo. (707 mg; 86%; M.P. 230°–240° C. (dec); LC-MS: 402 ($MH^+$); anal. RP18-HPLC RT: 5.35 min.).

EXAMPLE 30

[6-(2-Chloro-ethoxy)-7-(2-methoxy-ethoxy)-quinazolin-4-yl]-(3-ethynyl-phenyl)-amine Hydrochloride The title product was prepared from 4-chloro-6-(2-chloro-ethoxy)-7-(2-methoxyethoxy)-quinazoline (399 mg, 1.26 mmol) and 3-ethynyl-aniline (147 mg, 1.26 mmol) as described for Example 29. (515 mg; 94%; M.P. 215°–225° C. (dec); LC-MS: 398 ($MH^+$); anal. RP18-HPLC RT: 4.85 min.).

EXAMPLE 31

6,7-Bis(2-acetoxy-ethoxy)-4-(3-ethynyl-phenylamino)-quinazoline

The title product of Example 29 (200 mg, 0.456 mmol) was treated with cesuim acetate (1.75 g, 9.12 mmol) in DMF (3 mL) at 120° C. under an atmosphere of $N_2$ for 16 hours. The reaction mixture was partitioned between brine and $CHCl_3$, and the organic extract was washed with brine, dried over $Na_2SO_4$, filtered and concentrated in vacuo to afford an oil (277 mg) which was recrystallized from $CH_2Cl_2$/hexane. (184 mg; 90%; M.P. 137°–138° C.; LC-MS: 450 ($MH^+$); anal. RP18-HPLC RT: 4.64 min.).

EXAMPLE 32

2-[4-(3-Ethynyl-phenylamino)-7-(2-hydroxy-ethoxy)-quinazolin-6-yloxy]-ethanol Hydrochloride 6,7-Bis-(2-acetoxy-ethoxy)-4-(3-ethynyl-phenyl-amino)-quinazoline (199 mg, 0.443 mmol) in methanol (3 mL) was treated with 7M aqueous KOH (0.25 mL). The mixture was stirred at 20° C. for 2 hours before removing the solvent in vacuo. The solid residue was washed with water to remove salts, and dried azeotropically by dissolution two times in acetonitrile and concentration in vacuo to afford 116 mg of title product as its free base. This material was converted to its HCl salt according to the method used in Example 28 (115 mg; 65%; M.P.215°–218° C. (dec); LC-MS: 366 ($MH^+$); anal. RP18-HPLC RT: 3.08 min.).

EXAMPLE 33

6-(2-Acetoxy-ethoxy)-4-(3-ethynyl-phenylamino)-7-(2-methoxy-ethoxy)-quinazoline

The title product of Example 30 (160 mg, 0.368 mmol); was treated with cesium acetate (707 mg, 3.68 mmol) in DMF (3 mL) at 120° C. under an atmosphere of $N_2$ for 16 hours. The reaction mixture was partitioned between brine and $CHCl_3$, and the organic extract was washed with brine, dried over $Na_2SO_4$, filtered and concentrated in vacuo to afford a residue (285 mg) which was recrystallized from ethylacetate/hexane. (134 mg; M.P. 84°–87° C.; LC-MS: 422 ($MH^+$); anal. RP18-HPLC RT: 4.38 min.).

EXAMPLE 34

[7-(2-Chloro-ethoxy)-6-(2-methoxy-ethoxy)-quinazolin-4-yl]-(3-ethynyl-phenyl)-amine Hydrochloride This product was prepared from 4-chloro-7-(2-chloro-ethoxy)-6-(2-methoxy-ethoxy)-quinazoline (600 mg, 1.89 mmol) and 3-ethynyl-aniline (147 mg, 1.26 mmol) as described for Example 29. (737 mg; 90%; M.P. 225°–235° C. (dec); LC-MS: 398 (MH⁺); anal. RP18-HPLC RT: 4.89 min.).

EXAMPLE 35

7-(2-Acetoxy-ethoxy)-4-(3-ethynyl-phenylamino)-6-(2-methoxy-ethoxy)-quinazoline

The title product of Example 34 (160 mg, 0.368 mmol); was treated with cesium acetate (707 mg, 3.68 mmol) in DMF (3 mL) at 120° C. under an atmosphere of $N_2$ for 16 hours. The reaction mixture was partitioned between brine and $CHCl_3$, and the organic extract was washed with brine, dried over $Na_2SO_4$, filtered and concentrated in vacuo to afford a residue (288 mg) which was recrystallized from ethyl acetate/hexanes. (134 mg; M.P.134°–135° C.; LC-MS: 422 (MH⁺); anal. RP18-HPLC RT: 4.43 min.).

EXAMPLE 36

2-[4-(3-Ethynyl-phenylamino)-6-(2-methoxy-ethoxy)-quinazolin-7-yl-oxy]-ethanol Hydrochloride The title product of Example 35 (149 mg, 0.354 mmol) in methanol (3 mL) was treated with 5M aqueous KOH (0.25 mL). The mixture was stirred at 20° C. for 30 minutes before removing the solvent in vacuo. The solid residue was washed with water to remove salts, and dried azeotropically by dissolution two times in acetonitrile and concentration in vacuo to afford 100 mg of title product as its free base. This material was converted to its HCl salt according to the method used in Example 28 (87 mg; 59%; M.P. 230°–235° C. (dec); LC-MS: 380 (MH⁺); anal. RP18-HPLC RT: 3.42 min.).

EXAMPLE 37

(3-Ethynyl-phenyl)-{6-(2-methoxy-ethoxy)-7-[2-(4-methyl-piperazin-1-yl)-ethoxy]-quinazolin-4-yl}-amine Dihydrochloride The title product of Example 34 (110 mg, 0.253 mmol) in DMF (2 mL) was treated with N-methyl-piperazine (281 μL, 2.53 mmol) at 110° C. for 16 hours. The reaction mixture was partitioned between $CHCl_3$ and saturated aqueous $NaHCO_3$. The organic extracts were washed with brine, dried over $Na_2SO_4$, filtered and concentrated in vacuo. The crude product was chromatographed on silica using 15% methanol/$CH_2Cl_2$ to provide 56 mg of pure product as its free base. This white solid was dissolved in a minimum volume of $CHCl_3$, and titrated with 2 equivalents of 1M HCl in ether to precipitate the title product as a white solid (65 mg; 48%; M.P. 130°–142° C. (dec); LC-MS: 462 (MH⁺); anal. RP18-HPLC RT: 3.69 min.).

EXAMPLE 38

(3-Ethynyl-phenyl)-[7-(2-imidazol-1-yl-ethoxy)-6-(2-methoxy-ethoxy)quinazolin-4-yl]-amine Dihydrochloride The title product from Example 34 (110 mg, 0.253 mmol) in DMF (2 mL) was treated with imidazole (172 mg, 2.53 mmol) at 110° C. for 48 hours. The reaction mixture was partitioned between $CHCl_3$ and saturated aqueous $NaHCO_3$. The organic extracts were washed with brine, dried over $Na_2SO_4$, filtered and concentrated in vacuo. The crude product (119 mg) was chromatographed on silica using 10% methanol/$CH_2Cl_2$ to provide 85 mg of pure title product as its free base. This white solid was dissolved in a minimum volume of $CHCl_3$, and titrated with 2 equivalents of 1M HCl in ether to precipitate the title product as a white solid (95 mg; 75%; M.P. 220°–227° C. (dec); LC-MS: 430 (MH⁺); anal. RP18-HPLC RT: 3.75 min.).

EXAMPLE 39

(3-Ethynyl-phenyl)-[6-(2-imidazol-1-yl-ethoxy)-7-(2-methoxy-ethoxy)-quinazolin-4-yl]-amine Dihydrochloride The title product of Example 30 (110 mg, 0.253 mmol) in DMF (2 mL) was treated with imidazole (172 mg, 2.53 mmol) at 110° C. for 48 hours. The reaction mixture was partitioned between $CHCl_3$ and saturated aqueous $NaHCO_3$. The organic extracts were washed with brine, dried over $Na_2SO_4$, filtered and concentrated in vacuo. The crude product (125 mg) was chromatographed on silica using 10% methanol/$CH_2Cl_2$ to provide 86 mg of pure title product as its free base. This white solid was dissolved in a minimum volume of $CHCl_3$, and titrated with 2 equivalents of 1M HCl in ether to precipitate the title product as a white solid dihydrochloride salt (95 mg; 78%; M.P. 85°–100° C. (dec); LC-MS: 430 (MH⁺); anal. RP18-HPLC RT: 4.13 min.).

EXAMPLE 40

(3-Ethynyl-phenyl)-[7-(2-methoxy-ethoxy)-6-(2-morpholin-4-yl-ethoxy)-quinazolin-4-yl]-amine Dihydrochloride The title product from Example 30 (107 mg, 0.245 mmol) in DMF (2 mL) was treated with morpholine (214 μL, 2.45 mmol) at 80° C. for 24 hours. The reaction mixture was partitioned between $CHCl_3$ and saturated aqueous $NaHCO_3$. The organic extracts were washed with brine, dried over $Na_2SO_4$, filtered and concentrated in vacuo. The crude product (168 mg) was chromatographed on silica using 7.5% methanol/$CH_2Cl_2$ to provide 65 mg of pure title product as its free base. This white solid was dissolved in a minimum volume of $CHCl_3$, and titrated with 2 equivalents of 1M HCl in ether to precipitate the title product as a white solid (88 mg; 59%; M.P. 115°–130° C. (dec); LC-MS: 449 (MH⁺); anal. RP18-HPLC RT: 4.00 min.).

EXAMPLE 41

2-[4-(3-Ethynyl-phenylamino)-7-(2-methoxy-ethoxy)-quinazolin-6-yloxy]-ethanol Hydrochloride The title product from Example 33 (149 mg, 0.354 mmol) in methanol (3 mL) was treated with 5M aqueous KOH (0.25 mL). The mixture was stirred at 20° C. for 30 minutes before removing the solvent in vacuo. The solid residue was washed with water to remove salts, and dried azeotropically by dissolution two times in acetonitrile and concentration in vacuo to afford 95 mg of title product as its free base. This material was converted to its HCl salt according to the method used in Example 28 (89 mg; 61%; M.P. 190°–215° C. (dec); LC-MS: 380 (MH⁺); anal. RP18-HPLC RT: 3.66 min.).

EXAMPLE 42

(6,7-Diethoxy-quinazolin-4-yl)-(3-ethynyl-phenyl)-amine Hydrochloride 6,7-Diethoxyquinazolin-4-one (120 mg, 0.512 mmol), triphenylphosphine (295 mg, 1.126 mmol) and 3 mL of carbon tetrachloride were refluxed for 16 hours. The reaction mixture was concentrated in vacuo to a residue which was diluted with 3 mL of isopropyl alcohol and 3-ethynylaniline (66 mg, 0.563 mmol) and refluxed for 3 hours. The cooled reaction mixture was filtered to afford solid title product which was washed with 10 mL of isopropyl alcohol and dried in vacuo at 70° C., 140 mg (75%); mp 269°–270° C.

EXAMPLE 43

(6,7-Diethoxy-quinazolin-4-yl)-(3-ethynyl-2-methyl-phenyl)-amine Hydrochloride

4-Chloro-6,7-diethoxyquinazoline (200 mg, 0.792 mmol) and 3-(2'-trimethylsilylethynyl-2-methyl-aniline (168 mg, 0.871 mmol) in 4 mL of tert-butyl alcohol was refluxed for 16 hours. The cooled reaction mixture was diluted with 5 mL of ethyl ether and filtered to afford solid (6,7-diethoxy-quinazolin-4-yl)-(3-(2'-trimethylsilyl-ethynyl)-2-methyl-phenyl)-amine hydrochloride which was washed with 10 mL of ethyl ether and dried in vacuo at 70° C. This material was desilated directly by treatment with 2 mL of methanol containing 1 drop of water and 100 mg of potassium carbonate for 0.5 hours. The heterogeneous reaction mixture was filtered through Celite and vacuum evaporated to a residue which was dissolved in excess 1N HCl in methanol, precipitated with ethyl ether, filtered and dried in vacuo at 70° C. to afford the title product; 160 mg (75%); mp 258°–259.5° C.

EXAMPLE 44

(3-Ethynyl-phenyl)-(6-methyl-quinazolin-4-yl)-amine Hydrochloride

6-Methyl-quinazolin-4-one (350 mg, 2.18 mmol) was added to a suspension of polymer-supported triphenylphosphine (from Fluka, 3.63 g of about 3 mmol P/g resin; 10.9 mmol) in a mixture of $CCl_4$ (3.35 g, 21.80 mmol) and 1,2 dichloroethane (10 mL). The mixture was heated to 60° C. for 2 hours and then the polymer was removed by filtration and washed with dichloroethane. The filtrate was collected in a flask containing 3-ethynyl-aniline (0.644 g, 2.18 mmol) and concentrated to 5 mL by evaporation. After 4 hours reflux under $N_2$, followed by cooling to 20° C., the title product was collected by filtration (551 mg; 86%; M.P. 256°–257° C.; LC-MS: 260 (MH$^+$); anal. RP-HPLC RT: 4.41 min).

EXAMPLE 45

2-{2-[4-(3-Ethynyl-phenylamino)-6-(2-methoxy-ethoxy)-quinazolin-7-yloxy]-ethylsulfanyl}-propionic Acid Ammonium Salt The title product of Example 34 (150 mg, 0.34 mmol) was added to a solution of thiolactic acid (100 µL, 1.14 mmol) and KOH (150 mg, 2.7 mmol) in degassed DMF (5 mL)/$H_2O$ (0.5 mL). The reaction mixture was stirred at 50° C. under an atmosphere of $N_2$ for 72 hours and then cooled to room temperature. The pH of the mixture was adjusted to about 4.0 with acetic acid and then partitioned between $CHCl_3$ and brine. The organic extracts were washed with brine, dried over $Na_2SO_4$, filtered and concentrated in vacuo. The crude product was purified by preparative RP18 HPLC utilizing a gradient of 15% to 100% $CH_3CN$/pH 4.5, 50 mM ammonium acetate followed by lyophilization of the appropriate pure fractions to afford the title product (28 mg; 18%; M.P. 95°–103° C. (dec); LC-MS: 468 (MH$^+$); anal. RP-HPLC RT: 3.57 min).

EXAMPLE 46

{2-[4-(3-Ethynyl-phenylamino)-6-(2-methoxy-ethoxy)-quinazolin-7-yloxy]-ethylsulfanyl}-acetic Acid Ammonium Salt The title product was prepared from the title product of Example34 and mercaptoacetic acid according to the method of Example 45. (3%; LC-MS: 454 (MH$^+$); anal. RP-HPLC RT: 3.37 min).

EXAMPLE 47

4-(3-Ethynyl-phenylamino)-6-(2-methoxy-ethoxy)-quinazolin-7-ol

This product was isolated as a more lipophilic product (by preparative RP18 HPLC) from the reaction used to generate the title product of Example 46 (5%; LC-MS: 336 (MH$^+$); anal. RP-HPLC RT: 3.60 min).

EXAMPLE 48

(3-ethynyl-phenyl)-[7-(2-methoxy-ethoxy)-6-vinyloxy-quinazolin-4-yl]-amine and [6-(2-ethoxy-ethoxy)-7-(2-methoxy-ethoxy)-quinazolin-4-yl]-(3-ethnynl-phenyl)-amine Hydrochloride The title product of Example 30 (107 mg, 0.245 mmol) was treated with sodium ethoxide (0.582 mmol) in refluxing ethanol (3 mL) for 24 hours. The solvent was removed in vacuo and the product was isolated by flash chromatography on silica using 10% acetone/$CH_2Cl_2$ to provide 30 mg of the 6-vinyloxy product (33%; M.P. 113°–114° C.; LC-MS: 362 (MH$^+$); anal. RP-HPLC RT: 4.84 min). The 6-(2-ethoxy-ethoxy) derivative eluted as a more polar product (45 mg) and was converted to its HCl salt according to the procedure described for Example28 (43%; M.P. 220°–225° C. (dec); LC-MS: 408 (MH$^+$); anal. RP-HPLC RT: 4.35 min).

EXAMPLE 49

4-(3-Ethynyl-phenylamino)-7-(2-methoxy-ethoxy)-quinazolin-6-ol Hydrochloride (3-Ethynyl-phenyl)-[7-(2-methoxy-ethoxy)-6-vinyloxy-quinazolin-4-yl]-amine (20 mg; from Example 48) was hydrolyzed by treatment with 6M HCl/methanol (30:70; 3 mL) at 50° C. for 5 days. The solution was concentrated in vacuo, and the residue was partitioned between $CHCl_3$ and brine at a pH of about 7. The organic extracts were washed with brine, dried over $Na_2SO_4$, filtered and concentrated in vacuo to afford the title product as its free base (15 mg), which was converted to its HCl salt according to the procedure described for Example 28 (M.P. 135°–150° C. (dec); LC-MS: 336 (MH$^+$); anal. RP-HPLC RT: 3.77 min).

EXAMPLE 50

1-{2-[4-(3-Ethynyl-phenylamino)-6-(2-methoxy-ethoxy)-quinazolin-7-yloxy]-ethyl}-1H-pyridin-4-one Hydrochloride NaH (30 mg of 60% in mineral oil, 0.77 mmol) was added to anhydrous DMF (2.0 mL) followed by pyrid-4-one (79 mg, 0.83 mmol). The mixture was stirred 40 minutes at 22° C. until all solids dissolved and the evolution of $H_2$ ceased. The title product of Example 34 (120 mg, 0.28 mmol) and tetrabutylammonium iodide (15 mg) were added and the reaction mixture was stirred at 22° C. for 7 days under $N_2$. Additional pyrid-4-one (79 mg) and NaH (30 mg of 60%) were dissolved in DMF (2 mL) and the solution was added to the reaction mixture. After another 4 days stirring the mixture was partitioned between $CHCl_3$ and brine. The organic extracts were dried over $Na_2SO_4$, filtered and concentrated in vacuo. The crude product was purified by flash chromatography on silica utilizing 10% methanol/$CH_2Cl_2$ to afford 65 mg of the free base of the title product which was converted to the mono-hydrochloride salt according to the procedure described for Example 28 (66 mg; M.P. 240°–248° C. (dec); LC-MS: 457 (MH$^+$); anal. RP-HPLC RT: 3.23 min)

EXAMPLE 51

1-{2-[4-(3-Ethynyl-phenylamino)-7-(2-methoxy-ethoxy)-quinazolin-6-yloxy]-ethyl}-1H-pyridin-4-one Hydrochloride The free base of this product was prepared from the title product of Example 30 and the sodium salt of pyrid-4-one as described for Example 50. The free base was isolated by flash chromatography with 15% methanol/CHCl$_3$ and converted to the title product according to the procedure described for Example 28 (32%; M.P. 155°–168° C. (dec); LC-MS: 457 (MH$^+$); anal. RP-HPLC RT: 3.45 min).

EXAMPLE 52

(3-Ethynyl-phenyl)-(6-methoxy-quinazolin-4-yl)-amine Hydrochloride

A 25 mM solution of 6-methoxy-3H-quinazolin-4-one in 1,2-dichloroethane was added to polymer-supported triphenylphosphine (from Fluka, about 3 mmol P/g polymer; 2.5 mol equiv) and carbon tetrachloride (100 mole equiv). The reaction mixture was heated, with shaking, at 60° C. for 21 hours, cooled to 22° C., and a 30 mM solution of the 3-ethynylaniline (1.5 mole equiv) in t-butanol was added. The resulting mixture was then heated, with shaking, at 60° C. for 18 hours followed by cooling to 22° C. The polymer was filtered off and washed twice with methanol. The methanol washes were added to the filtrate and the solution was concentrated in vacuo to afford the title product (73%; LC-MS: 276 (MH$^+$); anal. RP18-HPLC RT: 5.82 min). For these cases the analytical RP18-HPLC system consisted of a Waters 717 (trademark) autosampler, Waters 996 Photodiode Array Detector (trademark), and Waters 600 quarternary solvent delivery system, and was controlled by Millennium (trademark) software. The aliquots of samples were chromatographed using a linear gradient of 0% to 100% acetonitrile/0.2M ammonium acetate buffer (pH 4.5) over ten minutes at a flow rate of 3 ml/min. using a Perkin-Elmer Pecosphere (trademark) (3 mm×3 cm) C18 column.

The compounds of Examples 53–94, as their hydrochloride salts, were prepared in an analogous manner to that of Example 52 from the appropriate 3H-quinazolin-4-one derivative and 3-ethynyl-aniline:

| Example | Product | % Yield | LC-MS (MH+) | HPLC RT (mins) |
|---|---|---|---|---|
| 53 | (6-Chloro-quinazolin-4-yl)-(3-ethynyl-phenyl)-amine | 60 | 280, 282 | 6.44 |
| 54 | [7-Chloro-6-(2,5-dichloro-phenylsulfanyl)-quinazolin-4-yl]-(3-ethynyl-phenyl)-amine | 51 | 456, 458 | 8.74 |
| 55 | 7-Chloro-4-(3-ethynyl-phenylamino)-quinazoline-6-carbonitrile | 12 | 305, 307 | 6.51 |
| 56 | [6-Bromo-7-(4-chloro-phenoxy)-quinazolin-4-yl]-(3-ethynyl-phenyl)-amine | 28 | 450, 452 | 8.05 |
| 57 | [6-(4-Bromo-benzylsulfanyl)-quinazolin-4-yl]-(3-ethynyl-phenyl)-amine | 50 | 446, 448 | 7.99 |
| 58 | (7-Bromo-6-methylsulfanyl-quinazolin-4-yl)-(3-ethynyl-phenyl)-amine | 46 | 370, 372 | 6.99 |
| 59 | {7-Chloro-6-[4-(4-chloro-phenylsulfanyl)-phenoxy]-quinazolin-4-yl}-(3-ethynyl-phenyl)-amine | 82 | 514, 516 | 9.45 |
| 60 | (3-Ethynyl-phenyl)-(7-phenylsulfanyl-quinazolin-4-yl)-amine | 88 | 354 | 7.40 |
| 61 | (3-Ethynyl-phenyl)-(6-iodo-quinazolin-4-yl)-amine | 64 | 372 | 6.81 |
| 62 | (3-Ethynyl-phenyl)-(6-0trifluoromethyl-quinazolin-4-yl)-amine | 53 | 314 | 6.73 |
| 63 | [7-Chloro-6-(4-chloro-phenoxy)-quinazolin-4-yl]-(3-ethynyl-phenyl)-amine | 78 | 406, 408 | 8.06 |
| 64 | [7-Chloro-6-(4-chloro-phenylsulfanyl)-quinazolin-4-yl]-(3-ethynyl-phenyl)-amine | 68 | 422, 424 | 8.45 |
| 65 | [7-Chloro-6-(4-methoxy-phenoxy)-quinazolin-4-yl]-(3-ethynyl-phenyl)-amine | 88 | 402, 404 | 7.55 |
| 66 | [7-Chloro-6-(4-fluoro-phenoxy)-quinazolin-4-yl]-(3-ethynyl-phenyl)-amine | 80 | 390 | 7.61 |
| 67 | [6-(4-Chloro-phenoxy)-quinazolin-4-yl]-(3-ethynyl-phenyl)-amine | 79 | 372, 374 | 7.66 |
| 68 | 7-Bromo-4-(3-ethynyl-phenylamino)-quinazoline-6-sulfonic acid | 61 | 431, 433 | 6.44 |
| 69 | (6-Bromo-7-chloro-quinazolin-4-yl0-(3-ethynyl-phenyl)-amine | 80 | 358, 360 | 7.17 |
| 70 | 4-(3-Ethynyl-phenylamino)-quinazoline-6-carbonitrile | 72 | 271 | 5.84 |
| 71 | [6-(4-Bromo-phenylsulfanyl)-7-chloro-quinazolin-4-yl]-(3-ethynyl-phenyl)-amine | 70 | 466, 468 | 8.56 |
| 72 | {6-[2-(4-Bromo-phenoxy)-ethylsulfanyl]-quinazolin-4-yl)-(3-ethynyl-phenyl)-amine | 79 | 476, 478 | 8.11 |
| 73 | 4-[7-Chloro-4-(3-ethynyl-phenylamino)-quinazolin-6-ylsulfanyl-methyl]-benzonitrile | 85 | 427, 429 | 7.56 |
| 74 | [7-Chloro-6-(3-chloro-phenoxy)-quinazolin-4-yl]-(3-ethynyl-phenyl)-amine | 80 | 406, 408 | 8.10 |
| 75 | [6-(3-Bromo-phenoxy)-7-chloro-quinazolin-4-yl]-(3-ethynyl-phenyl)-amine | 82 | 450, 452 | 8.22 |
| 76 | (7-Chloro-6-phenoxy-quinazolin-4-yl)-3-ethynyl-phenyl)-amine | 83 | 372, 374 | 7.59 |

-continued

| Example | Product | % Yield | LC-MS (MH+) | HPLC RT (mins) |
|---|---|---|---|---|
| 77 | [7-Chloro-6-(4-methylsulfanyl-phenoxy)-quinazooin-4-yl]-(3-ethynyl-phenyl)-amine | 86 | 418, 420 | 8.02 |
| 78 | [7-Chloro-6-(4-methanesulfonyl-phenoxy)-quinazolin-4-yl]-(3-ethynyl-phenyl)-amine | 73 | 450, 452 | 6.73 |
| 79 | (7-Chloro-6-p-tolyloxy-quinazolin-4-yl]-(3-ethynyl-phenyl)-amine | 85 | 386, 388 | 7.95 |
| 80 | (e-Ethynyl-phenyl)-[6-(4-phenoxy-phenoxy)-quinazoin-4-yl]-amine | 81 | 430 | 8.29 |
| 81 | (7-Chloro-6-phenylsulufanyl-quinazolin-4-yl)-(3-ethynyl-phenyl)-amine | 80 | 388, 390 | 7.96 |
| 82 | [6-(3-Chloro-phenoxy)-quinazoin-4-yl]-(3-ethynyl-phenyl)-amine | 77 | 372, 374 | 7.71 |
| 83 | [6-(3,5-Dichloro-phenoxy)-quinazolin-4-yl]-(3-ethynyl-phenyl)-amine | 61 | 406, 408 | 8.30 |
| 84 | [6-(2-Chloro-phenoxy)-quinazolin4-yl]-(3-ethynyl-phenyl)-amine | 70 | 372, 374 | 7.38 |
| 85 | (7-Chloro-6-methanesulfonyl-quinazooin-4-yl)-(3-ethynyl-phenyl)-amine | 74 | 358, 360 | 5.74 |
| 86 | [6-(3,4-Dichloro-phenoxy)-quinazolin-4-yl]-(3-ethynyl-phenyl)-amine | 62 | 406, 408 | 8.14 |
| 87 | [6-(4-Bromo-phenoxy)-quinazolin-4-yl]-(3-ethynyl-phenyl)-amine | 68 | 416, 418 | 7.81 |
| 88 | [6-(4-Chloro-2-methyl-phenoxy)-quinazolin-4-yl]-(3-ethynyl-phenyl)-amine | 73 | 386, 388 | 8.02 |
| 89 | [7-Chloro-4-(3-ethynyl-phenylamino)-quinazolin-6-ylsulfanyl]-acetonitrile** | 70 | 351 | 6.44 |
| 90 | (6-Allylsulfanyl-quinazolin-4-yl)-(3-ethynyl-phenyl)-amine | 72 | 318 | 6.93 |
| 91 | (7-Chloro-6-propylsulfanyl-quinazolin-4-yl)-(3-ethynyl-phenyl)-amine | 69 | 354, 356 | 7.79 |
| 92 | (7-Chloro-6-methyl-sulfanyl-quinazolin-4-yl)-(3-ethynyl-phenyl)-amine | 72 | 326, 328 | 6.94 |
| 93 | [7-Chloro-6-(2-methyl-sulfanyl-ethylsulfanyl)-quinazolin-4-yl]-(3-ethynyl-phenyl)-amine | 71 | 386, 388 | 7.56 |
| 94 | (6-Chloro-7-methoxy-quinaolin-4-yl)-(3-ethynyl-phenyl)-amine | 87 | 310, 312 | 6.65 |

**[7-Chloro-4-(3-ethynyl-phenylamino)-quinazolin-6-ylsulfanyl]-acetonitrile was obtained from 2-(7-chloro-4-oxo-3,4-dihydro-quinazolin-6-ylsulfanyl)-acetamide under these conditions.

EXAMPLE 95

(6,7-Dibutoxy-quinazolin-4-yl)-(3-ethynyl-phenyl)-amine Hydrochloride 6,7-Dibutoxyquinazolin-4-one (105 mg, 0.362 mmol), triphenylphosphine (208 mg, 0.796 mmol) and 5 mL of carbon tetrachloride were refluxed for 16 hours and the reaction mixture was concentrated in vacuo to a residue which was diluted with 3 mL of isopropyl alcohol and 3-ethynylaniline (47 mg, 0.398 mmol) and refluxed for 3 hours. The cooled reaction mixture was filtered to afford solid (6,7-dibutoxy-quinazolin-4-yl)-(3-ethynyl-phenyl)-amine hydrochloride which was washed with 10 mL of isopropyl alcohol and dried in vacuo at 70° C., 92 mg (60%); mp 247°–248° C.

EXAMPLE 96

(6,7-Diisopropoxy-quinazolin-4-yl)-(3-ethynyl-phenyl)-amine Hydrochloride 6,7-Diisopropoxyquinazolin-4-one (55 mg, 0.210 mmol), triphenylphosphine (121 mg, 0.462 mmol) and 3 mL of carbon tetrachloride were refluxed for 16 hours and the reaction mixture was concentrated in vacuo to a residue which was diluted with 3 mL of isopropyl alcohol and 3-ethynylaniline (30 mg, 0.257 mmol) and refluxed for 3 hours. The cooled reaction mixture was vacuum evaporated to afford the solid title product which was column chromatographed on silica gel eluted with 5% acetone in methylene chloride containing 0.25% triethylamine. Fractions containing the pure product were concentrated in vacuo to a solid which was dissolved in 2 mL of 1N HCl in methanol, precipitated with ethyl ether, filtered and dried in vacuo at 70° C. to afford the title product; 140 mg (75%); mp 241°–242° C.

EXAMPLE 97

(6-Chloro-7-(2-methoxyethylsulfanyl)-quinazolin-4-yl)-(3-ethynyl-phenyl)-amine Hydrochloride 6-Chloro-7-(2-methoxyethylsulfanyl)-quinazolin-4-one (200 mg, 0.739 mmol), triphenylphosphine (427 mg, 1.63 mmol) and 0.7 mL of carbon tetrachloride were refluxed in 4 ml of 1,2-dichloroethane for 4 hours, concentrated in vacuo to a residue, diluted with 4 mL of isopropyl alcohol and 3-ethynylaniline (129 mg, 1.104 mmol) and refluxed for 16 hours. The hot reaction mixture was filtered to isolate crude product which was column chromatographed on silica gel eluted with 5% methanol in chloroform. Fractions containing the pure product were concentrated in vacuo to afford the title product as a solid; 23 mg (8.4%); mp 230°–232° C.

EXAMPLE 98

(6,7-Bis-[2-methoxyethoxy]-quinazolin-4-yl)-(3-ethynyl-2-methyl-phenyl)-amine 6,7-Bis-[2-methoxyethoxy]-4-chloro-quinazoline (90 mg, 0.288 mmol) and 3-(2'-trimethylsilylethynyl-2-methylaniline (62 mg, 0.317 mmol) were refluxed in 4 mL of tert-butyl alcohol for 16 hours. The cooled reaction mixture was diluted with 1 mL of isopropyl alcohol and filtered to afford solid (6,7-bis-(methoxyethoxy)-quinazolin-4-yl)-(3-(2'-trimethylsilyl-ethyn-1yl)-2-methyl-phenyl)-amine hydrochloride which was washed with 10 mL of ethyl ether and dried in vacuo at 70° C.; 70 mg. Of this material 51 mg was desilated by treatment with in 3 mL of methanol containing 1 drop of water and 50 mg of potassium carbonate for 0.5 hours at room temperature. The heterogeneous reaction mixture was filtered through celite and vacuum evaporated to a residue which was dried in vacuo at 70° C. to afford the title product as a dry foam; 38 mg (75%); mp 232° C.

EXAMPLE 99

(6,7-Bis-[2-methoxyethoxy]-quinazolin-4-yl)-(3-ethynyl-5'-fluoro-phenyl)-amine Hydrochloride 6,7-Bis[2-methoxyethoxy]-4-chloro-quinazoline (90 mg, 0.288 mmol) and 3-(2'-trimethylsilylethynyl-5-fluoro-aniline (69 mg, 0.317 mmol) were refluxed in 3 mL of tert-butyl alcohol for 5 hours. The cooled reaction mixture was diluted with 2 mL of isopropyl alcohol and filtered to afford solid (6,7-bis-methoxyethoxy-quinazolin-4-yl)-(3-(2'-trimethylsilyl-ethynyl)-5'-fluoro-phenyl)-amine hydrochloride which was washed with 10 mL of ethyl ether and dried in vacuo at 70° C.; 131 mg. All of this material was desilated by dissolution in 3 mL of methanol containing 1 drop of water and 35 mg of potassium carbonate for 0.5 hours at room temperature. The reaction mixture was adjusted to pH 2.5 with aqueous 1N hydrochloric acid and filtered. The solid was dried in vacuo at 70° C. to afford the title product; 92 mg (78%); mp 249°–250° C.

EXAMPLE 100

(7-Propylsulfanyl-quinazolin-4-yl)-(3-ethynyl-phenyl)-amine Hydrochloride

7-Propylsulfanyl-quinazolin-4-one (300 mg, 1.36 mmol), triphenylphosphine (785 mg, 2.99 mmol), 1.31 mL of carbon tetrachloride and 5 mL of chloroform were refluxed for 16 hours and the reaction mixture was concentrated in vacuo to a residue which was diluted with 5 mL of isopropyl alcohol and 3-ethynylaniline (175 mg, 1.49 mmol) and refluxed for 3 hours. The cooled reaction mixture was concentrated in vacuo and the residue purified by column chromatography on silica gel eluted with 10% methanol in chloroform. Fractions containing the pure title product, as the frree amine, were concentrated in vacuo to afford solid which was added to 3 mL of 1N HCl in methanol. This solution was evaporated in vacuo to a residue which was triturated with 4 mL of hot isopropyl alcohol cooled and filtered. The solid thus obtained was dried in vacuo at 70° C. to afford pure title product; 239 mg (55%); mp 229°–230° C.

EXAMPLE 101

[7-(2-Methoxyethylsulfanyl)-quinazolin-4-yl]-(3-ethynyl-phenyl)-amine Hydrochloride In the same manner as Example 42 [7-(2-methoxyethylsulfanyl)-quinazolin-4-yl]-(3-ethynyl-phenyl)-amine hydrochloride was prepared from 7-(2-methoxyethylsulfanyl)-quinazolin-4-one (200 mg, 0.847 mmol), triphenylphosphine (533 mg, 2.03 mmol) and 3 mL of carbon tetrachloride in 74% yield; 233 mg; mp 208°–209° C.

EXAMPLE 102

(7-Chloro-6-nitro-quinazolin-4-yl)-(3-ethynyl-phenyl)-amine Hydrochloride

7-Chloro-6-nitro-quinazolin-4-one (1.002 g, 4.44mmol), phosphorous oxychloride (11.5 g, 7.51 mmol) and phosphorous pentachloride (1.62 g, 7.74 mmol) were refluxed for 2 hours and the reaction mixture was concentrated in vacuo to a residue which was triturated with toluene and then again with chloroform and dried in vacuo to afford crude 4,7-dichloro-6-nitro-quinazoline. This was dissolved in 35 mL of isopropyl alcohol and 3-ethynylaniline (639 mg, 5.45 mmol) and refluxed for 3 hours. The cooled reaction mixture was filtered to afford the title product as a solid which was washed with 10 mL of isopropyl alcohol and dried in vacuo at 70° C., 1.055 g (66%); mp 230.8°–232.6° C.

EXAMPLE 103

(6-Amino-7-chloro-quinazolin-4-yl)-(3-ethynyl-phenyl)-amine Hydrochloride (7-Chloro-6-nitro-quinazolin-4-yl)-(3-ethynyl-phenyl)-amine hydrochloride (166 mg, 0.295 mmol) and sodium dithionite (207 mg, 1.19 mmol) were stirred in 1.5 mL of formic acid for 4 hours at room temperature. 45 mL of methanol were added to the reaction mixture which was set aside for 16 hours at room temperature. The precipitate thus obtained was filtered, triturated with 3% sodium bicarbonate for 0.5 hours and refiltered. The solid was dissolved in 20 mL of 1N HCl in methanol and precipitated with 200 mL of ethyl ether. This was filtered and dried in vacuo at 70° C. to afford the title product, 72 mg (83%); mp 260°–265° C.

EXAMPLE 104

(3-Ethynyl-phenyl)-(7-methoxy-6-nitro-quinazolin-4-yl)-amine (7-Chloro-6-nitroquinazolin-4-yl)-(3-ethynyl-phenyl)-amine hydrochloride (100 mg, 0.306 mmol and dry sodium methoxide (120 mg, 2.22 mmol) were stirred in 2 mL of dry 2-methylpyrrolidin-1-one for 8 hours at 30° C. To the cooled reaction mixture 0.93 mL of 3N and 1 mL of water were added. The mixture was diluted with 60 mL of water and extracted with two time 60 mL of ethyl acetate. The pooled organic layers were washed with three times 50 mL of water and 50 mL of brine, dried with magnesium sulfate, filtered and vacuum evaporated to afford the title product as a solid; 80 mg (82%); mp 213°–218° C. dec.

EXAMPLE 105

{2-[4-(3-Ethynyl-phenylamino)-7-(2-methoxy-ethoxy)-quinazolin-6-yloxy]-ethylsulfanyl}-acetic Acid Ammonium Salt This product was prepared from the title product of Example 30 and mercaptoacetic acid at 22° C. over 10 days according to the method outlined in Example 45. (16%; M.P. 98°–113° C. (dec); LC-MS 454 (MH$^+$); anal. RP-HPLC 3.24 min.)

PREPARATION 1

6,7-Bis(2-methoxy-ethoxy)-quinazolone

To ethyl 3,4-dihydroxybenzoate (36.4 g, 0.200 mol), $K_2CO_3$ (60.8 g, 0.44 mol) and tetrabutylammonium iodide (750 mg) in degassed acetone (400 mL) was added 2-bromoethyl methyl ether (69.5 g, 47 mL). The mixture was stirred under $N_2$ at reflux for 64 hours. Ether (600 mL) was added to the mixture and after stirring 30 minutes at 20° C. the precipitated salts were removed by filtration. The filtrate was concentrated in vacuo and the residue was triturated with hexane (500 mL) for 30 minutes and the white solid ethyl 3,4-bis(2-methoxy-ethoxy)benzoate was filtered and dried in vacuo (55.5 g; 93%; M.P. 50°–51° C.). A portion of this product (45.7 g, 0.158 mol) in acetic acid (150 mL) was treated dropwise with conc. $HNO_3$ (40 mL) at 5° C. and the solution stirred 24 hours before pouring into cold $H_2O$ (1.6 L). The mixture was extracted with ethyl acetate (1.1 L), and the organic phase was washed three times with 200 mL $H_2O$, and brine, dried over $Na_2SO_4$, filtered and concentrated in vacuo to afford ethyl 4,5-bis-(2-methoxy-ethoxy)-2-nitro-benzoate (54.3 g) as a brown oil. This nitro product (52.0 g, 0.15 mol) was dissolved in ethanol (1000 mL) containing 1 equivalent of HCl (generated in the ethanol by prior addition of 11 mL acetyl chloride), $PtO_2.H_2O$ (1.0 g) was added, and the mixture was hydrogenated under 45 psi $H_2$ for 6 hours. The catalyst was removed by filtration through Celite, and the filtrate was concentrated in vacuo to a thick slurry which was diluted with ether (400 mL). The solid white hydrochloride salt of ethyl 2-amino-4,5-bis-(2-methoxy-ethoxy)benzoate was filtered and dried in vacuo (44.7 g; 88%). A portion of this material (42 g, 0.12 mol) and ammonium formate (7.6 g, 0.12 mol) were disssolved in formamide (63 mL) and the stirred mixture was heated to 160°–165° C. under an atmosphere of $N_2$ for 3 hours. $H_2O$ (200 mL) was added and after cooling the precipitated crude title product was recovered by filtration, washed with cold $H_2O$, and dried in vacuo. The filtrate was extracted five times with $CHCl_3$, and the pooled organic extracts were washed with brine, dried over $Na_2SO_4$, and concentrated in vacuo. The residue and crude quinazolone precipitate were combined, triturated in hot acetonitrile (250 mL) for 30 minutes, cooled to 20° C. and treated with ether (250 mL). After cooling to 4° C. the white solid was filtered and dried in vacuo (30.4 g, 86%; GC-MS m/z 294 ($M^+$)).

PREPARATION 2

4-Chloro-6,7-bis-(2-methoxy-ethoxy)-quinazoline

To 6,7-bis(2-methoxy-ethoxy)-quinazolone (500 mg, 1.7 mmol), from Preparation 1, in $CHCl_3$ (10 mL) containing one drop of DMF was added oxalylchloride (490 µL, 5.6 mmol) in several portions over 5 minutes. Once foaming ceased the solution was refluxed 1.5 hours. The solvent was removed in vacuo and the residue was dissolved in 1,2-dichloroethane (20 mL) and washed two times with 80 mL saturated aqueous $Na_2CO_3$. The organic phase was dried over $Na_2SO_4$, and concentrated in vacuo to afford solid title product (520 mg, 92%; M.P. 108°–109° C.).

PREPARATION 3

4-Chloro-6,7-bis-(2-chloro-ethoxy)-quinazoline, 4-chloro-6-(2-chloro-ethoxy)-7-(2-methoxy-ethoxy)-quinazoline and 4-chloro-6,7-bis-(2-methoxy-ethoxy)-quinazoline and 4-chloro-7-(2-chloro-ethoxy)-6-(2-methoxy-ethoxy)-quinazoline 6,7-Bis(2-methoxy-ethoxy)-quinazolone (5.4 g, 18.3 mmol), from Preparation 1, and pyridine (3.0 mL, 37 mmol) were heated in refluxing $POCl_3$ (22 mL) under an atmosphere of dry nitrogen for 2.5 hours. Following concentration of the mixture in vacuo at 60° C. the residue was dissolved in $CHCl_3$ (150 mL) and carefully added in portions with stirring to cold saturated aqueous $NaHCO_3$ (100 mL). The mixture was stirred 10 min. after the addition was complete and the organic phase was separated, washed with brine, dried over $Na_2SO_4$, and concentrated in vacuo. The residue was flash chromatographed on silica using a gradient of 20% to 60% ethyl acetate/hexanes to afford 3.41 g of 4-chloro-6,7-bis-(2-methoxy-ethoxy)-quinazoline, 234 mg of 4-chloro-6-(2-chloro-ethoxy)-7-(2-methoxy-ethoxy)-quinazoline, 532 mg of 4-chloro-7-(2-chloro-ethoxy)-6-(2-methoxy-ethoxy)-quinazoline, and 330 mg of 4-chloro-6,7-bis-(2-chloroethoxy)-quinazoline.

We claim:

1. A compound of the formula

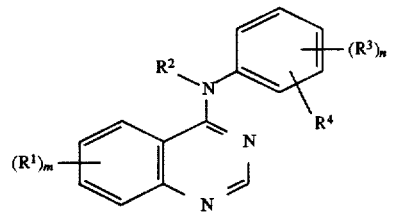

or a pharmaceutically acceptable salt thereof wherein:
X is halo or hydroxy;
m is 1, 2, or 3;
each $R^1$ is independently selected from the group consisting of hydrogen, halo, hydroxy, hydroxyamino, carboxy, nitro, guanidino, ureido, cyano, trifluoromethyl, and -($C_1$-$C_4$ alkylene)-W-(phenyl) wherein W is a single bond, O, S or NH;
or each $R^1$ is independently selected from $R^9$ and $C_1$-$C_4$ alkyl substituted by cyano, wherein $R^9$ is selected from the group consisting of $R^5$, —$OR^6$, —$NR^6R^6$, —C(O)$R^7$, —$NHOR^5$, —OC(O)$R^6$, cyano, A and —$YR^5$; $R^5$ is $C_1$-$C_4$ alkyl; $R^6$ is independently hydrogen or $R^5$; $R^7$ is $R^5$, —$OR^6$ or —$NR^6R^6$; A is selected from piperidino, morpholino, pyrrolidino, 4-$R^6$-piperazin-1-yl, imidazol-1-yl, 4-pyridon-1-yl, -($C_1$-$C_4$ alkylene) ($CO_2H$), phenoxy, phenyl, phenylsulfanyl, $C_2$-$C_4$ alkenyl, and -($C_1$-$C_4$ alkylene)C(O)$NR^6R^6$; and Y is S, SO, or $SO_2$; wherein the alkyl moieties in $R^5$, —$OR^6$ and —$NR^6R^6$ are optionally substituted by one to three halo substituents and the alkyl moieties in $R^5$, —$OR^6$ and —$NR^6R^6$ are optionally substituted by 1 or 2 $R^9$ groups, and wherein the alkyl moieties of said optional substituents are optionally substituted by halo or $R^9$, with the proviso that two heteroatoms are not attached to the same carbon atom;
or each $R^1$ is independently selected from —$NHSO_2R^5$, phthalimido-($C_1$-$C_4$) -alkylsulfonylamino, benzamido, benzenesulfonylamino, 3-phenylureido, 2-oxopyrrolidin-1-yl, 2,5-dioxopyrrolidin-1-yl, and $R^{10}$-($C_2$-$C_4$) -alkanoylamino wherein $R^{10}$ is selected from halo, —$OR^6$, $C_2$-$C_4$ alkanoyloxy, —C(O)$R^7$, and —$NR^6R^6$; and wherein said —$NHSO_2R^5$, phthalimido-($C_1$-$C_4$-alkylsulfonylamino, benzamido, benzenesulfonylamino, 3-phenylureido, 2-oxopyrrolidin-1-yl, 2,5-dioxopyrrolidin-1-yl, and $R^{10}$-($C_2$-$C_4$)-alkanoylamino $R^1$ groups are optionally substituted by 1 or 2 substituents independently selected from halo, $C_1$-$C_4$ alkyl, cyano, methanesulfonyl and $C_1$-$C_4$ alkoxy;
or two $R^1$ groups are taken together with the carbons to which they are attached to form a 5–8 membered ring that includes 1 or 2 heteroatoms selected from O, S and N;

39

R² is hydrogen or $C_1$-$C_6$ alkyl optionally substituted by 1 to 3 substituents independently selected from halo, $C_1$-$C_4$ alkoxy, —NR⁶R⁶, and —SO₂R⁵;

n is 1 or 2 and each R³ is independently selected from hydrogen, halo, hydroxy, $C_1$-$C_6$ alkyl, —NR⁶R⁶, and $C_1$-$C_4$ alkoxy, wherein the alkyl moieties of said R³ groups are optionally substituted by 1 to 3 substituents independently selected from halo, $C_1$-$C_4$ alkoxy, —NR⁶R⁶, and —SO₂R ; and, R⁴ is azido or -(ethynyl)-R¹¹ wherein R¹¹ is hydrogen or $C_1$-$C_6$ alkyl optionally substituted by hydroxy, —OR⁶, or —NR⁶R⁶.

2. The compound according to claim 1 wherein R² is hydrogen and R⁴ is -(ethynyl)-R¹¹.

3. A pharmaceutical composition for the treatment of a hyperproliferative disorder in a mammal which comprises a pharmaceutically effective amount of the compound of claim 1 and a pharmaceutically acceptable carrier.

4. The compound of claim 1 wherein each R¹ is independently selected from hydrogen, hydroxy, hydroxyamino, nitro, carbamoyl, ureido, R⁵ optionally substituted with halo, —OR⁶, carboxy, or —C(O)NH₂; —OR⁵ optionally substituted with halo, —OR⁶, —OC(O)R⁶, —NR⁶R⁶, or A; —NR⁶R⁶, —C(O)NR⁶R⁶, —SR⁵, phenyl-($C_2$-$C_4$)-alkoxy wherein said phenyl moiety is optionally substituted with 1 or 2 substituents independently selected from halo, R⁵ or —OR⁵.

5. The compound according to claim 1 wherein R² is hydrogen and R⁴ is azido.

6. The compound of claim 1 wherein R³ is halo and R¹ is hydrogen or —OR⁵.

7. The compound of claim 6 wherein R¹ is methoxy.

8. The compound of claim 1 selected from the group consisting of:

(6,7-dimethoxyquinazolin-4-yl)-(3-ethynylphenyl)-amine;

(6,7-dimethoxyquinazolin-4-yl)-[3-(3'-hydroxypropyn-1-yl)phenyl]-amine;

[3-(2'-(aminomethyl)-ethynyl)phenyl]-(6,7-dimethoxyquinazolin-4-yl)-amine;

(3-ethynylphenyl)-(6-nitroquinazolin-4-yl)-amine;

(6,7-dimethoxyquinazolin-4-yl)-(4-ethynylphenyl)-amine;

(6,7-dimethoxyquinazolin-4-yl)-(3-ethynyl-2-methylphenyl)-amine;

(6-aminoquinazolin-4-yl)-(3-ethynylphenyl)-amine;

(3-ethynylphenyl)-(6-methanesulfonylaminoquinazolin-4-yl)-amine;

(3-ethynylphenyl)-(6,7-methylenedioxyquinazolin-4-yl)-amine;

(6,7-dimethoxyquinazolin-4-yl)-(3-ethynyl-6-methylphenyl)-amine;

(3-ethynylphenyl)-(7-nitroquinazolin-4-yl)-amine;

(3-ethynylphenyl)-[6-(4'-toluenesulfonylamino)quinazolin-4-yl]-amine;

(3-ethynylphenyl)-{6-[2'-phthalimido-eth-1'-yl-sulfonylamino]quinazolin-4-yl}-amine;

(3-ethynylphenyl)-(6-guanidinoquinazolin-4-yl)-amine;

(7-aminoquinazolin-4-yl)-(3-ethynylphenyl)-amine;

(3-ethynylphenyl)-(7-methoxyquinazolin-4-yl)-amine;

(6-carbomethoxyquinazolin-4-yl)-(3-ethynylphenyl)-amine;

(7-carbomethoxyquinazolin-4-yl)-(3-ethynylphenyl)-amine;

40

[6,7-bis(2-methoxyethoxy)quinazolin-4-yl]-(3-ethynylphenyl)-amine;

(3-azidophenyl)-(6,7-dimethoxyquinazolin-4-yl)-amine;

(3-azido-5-chlorophenyl)-(6,7-dimethoxyquinazolin-4-yl)-amine;

(4-azidophenyl)-(6,7-dimethoxyquinazolin-4-yl)-amine;

(3-ethynylphenyl)-(6-methansulfonyl-quinazolin-4-yl)-amine;

(6-ethansulfanyl-quinazolin-4-yl)-(3-ethynylphenyl)-amine (6,7-dimethoxy-quinazolin-4-yl)-(3-ethynyl-4-fluorophenyl)-amine;

(6,7-dimethoxy-quinazolin-4-yl)-[3-(propyn-1'-yl)-phenyl]-amine;

[6,7-bis-(2-methoxy-ethoxy)-quinazolin-4-yl]-(5-ethynyl-2-methyl-phenyl)-amine;

[6,7-bis-(2-methoxy-ethoxy)-quinazolin-4-yl]-(3-ethynyl-4-fluoro-phenyl)-amine;

[6,7-bis-(2-chloro-ethoxy)-quinazolin-4-yl]-(3-ethynylphenyl)-amine;

[6-(2-chloro-ethoxy)-7-(2-methoxy-ethoxy)-quinazolin-4-yl]-(3-ethynyl-phenyl)-amine;

[6,7-bis-(2-acetoxy-ethoxy)-quinazolin-4-yl]-(3-ethynylphenyl)-amine;

2-[4-(3-ethynyl-phenylamino)-7-(2-hydroxy-ethoxy)-quinazolin-6-yloxy]-ethanol;

[6-(2-acetoxy-ethoxy)-7-(2-methoxy-ethoxy)-quinazolin-4-yl]-(3-ethynyl-phenyl)-amine;

[7-(2-chloro-ethoxy)-6-(2-methoxy-ethoxy)-quinazolin-4-yl]-(3-ethynyl-phenyl)-amine;

[7-(2-acetoxy-ethoxy)-6-(2-methoxy-ethoxy)-quinazolin-4-yl]-(3-ethynyl-phenyl)-amine;

2-[4-(3-ethynyl-phenylamino)-6-(2-hydroxy-ethoxy)-quinazolin-7-yloxy]-ethanol;

2-[4-(3-ethynyl-phenylamino)-7-(2-methoxy-ethoxy)-quinazolin-6-yloxy]-ethanol;

2-[4-(3-ethynyl-phenylamino)-6-(2-methoxy-ethoxy)-quinazolin-7-yloxy]-ethanol;

[6-(2-acetoxy-ethoxy)-7-(2-methoxy-ethoxy)-quinazolin-4-yl]-(3-ethynyl-phenyl)-amine;

(3-ethynyl-phenyl)-{6-(2-methoxy-ethoxy)-7-[2-(4-methyl-piperazin-1-yl)-ethoxy]-quinazolin-4-yl}-amine;

(3-ethynyl-phenyl)-[7-(2-methoxy-ethoxy)-6-(2-morpholin-4-yl)-ethoxy)-quinazolin-4-yl]-amine;

(6,7-diethoxyquinazolin-1-yl)-(3-ethynylphenyl)-amine;

(6,7-dibutoxyquinazolin-1-yl)-(3-ethynylphenyl)-amine;

(6,7-diisopropoxyquinazolin-1-yl)-(3-ethynylphenyl)-amine;

(6,7-diethoxyquinazolin-1-yl)-(3-ethynyl-2-methylphenyl)-amine;

[6,7-bis-(2-methoxy-ethoxy)-quinazolin-1-yl]-(3-ethynyl-2-methyl-phenyl)-amine;

(3-ethynylphenyl)-[6-(2-hydroxy-ethoxy)-7-(2-methoxy-ethoxy)-quinazolin-1-yl]-amine;

[6,7-bis-(2-hydroxy-ethoxy)-quinazolin-1-yl]-(3-ethynylphenyl)-amine; and

2-[4-(3-ethynyl-phenylamino)-6-(2-methoxy-ethoxy)-quinazolin-7-yloxy]-ethanol.

9. The compound of claim 1 selected from the group consisting of

41

(6,7-dipropoxy-quinazolin-4-yl)-(3-ethynyl-phenyl)-amine;

(6,7-diethoxy-quinazolin-4-yl)-(3-ethynyl-5-fluoro-phenyl)-amine;

(6,7-diethoxy-quinazolin-4-yl)-(3-ethynyl-4-fluoro-phenyl)-amine;

(6,7-diethoxy-quinazolin-4-yl)-(5-ethynyl-2-methyl-phenyl)-amine;

(6,7-diethoxy-quinazolin-4-yl)-(3-ethynyl-4-methyl-phenyl)-amine;

(6-aminomethyl-7-methoxy-quinazolin-4-yl)-(3-ethynyl-phenyl)-amine;

(6-aminomethyl-7-methoxy-quinazolin-4-yl)-(3-ethynylphenyl)-amine;

(6-aminocarbonylmethyl-7-methoxy-quinazolin-4-yl)-(3-ethynylphenyl)-amine;

(6-aminocarbonylethyl-7-methoxy-quinazolin-4-yl)-(3-ethynylphenyl)-amine;

(6-aminocarbonylmethyl-7-ethoxy-quinazolin-4-yl)-(3-ethynylphenyl)-amine;

(6-aminocarbonylethyl-7-ethoxy-quinazolin-4-yl)-(3-ethynylphenyl)-amine;

(6-aminocarbonylmethyl-7-isopropoxy-quinazolin-4-yl)-(3-ethynylphenyl)-amine;

(6-aminocarbonylmethyl-7-propoxy-quinazolin-4-yl)-(3-ethynylphenyl)-amine;

(6-aminocarbonylmethyl-7-methoxy-quinazolin-4-yl)-(3-ethynylphenyl)-amine;

(6-aminocarbonylethyl-7-isopropoxy-quinazolin-4-yl)-(3-ethynylphenyl)-amine; and (6-aminocarbonylethyl-7-propoxy-quinazolin-4-yl)-(3-ethynylphenyl)-amine.

10. The compound of claim 1 selected from the group consisting of:

(6,7-diethoxyquinazolin-1-yl)-(3-ethynylphenyl)-amine;

(3-ethynylphenyl)-[6-(2-hydroxy-ethoxy)-7-(2-methoxy-ethoxy)-quinazolin-1-yl]-amine;

[6,7-bis-(2-hydroxy-ethoxy)-quinazolin-1-yl]-(3-ethynylphenyl)-amine;

[6,7-bis-(2-methoxy-ethoxy)-quinazolin-1-yl]-(3-ethynylphenyl)-amine;

(6,7-dimethoxyquinazolin-1-yl)-(3-ethynylphenyl)-amine;

(3-ethynylphenyl)-(6-methanesulfonylamino-quinazolin-1-yl)-amine; and, (6-amino-quinazolin-1-yl)-(3-ethynylphenyl)-amine.

11. A pharmaceutical composition for the treatment of a hyperproliferative disorder in a mammal which comprises a therapeutically-effective amount of the compound of claim 1 and a pharmaceutically acceptable carrier.

12. A method of treating a hyperproliferative disorder in a mammal which comprises administering to said mammal a therapeutically-effective amount of the compound of claim 1.

13. The method of claim 12 wherein said hyperproliferative disorder is cancer.

14. The method of claim 13 wherein said cancer is brain, lung, squamous cell, bladder, gastric, pancreatic, breast, head, neck, oesophageal, gynecological or thyroid cancer.

15. The method of claim 12 wherein the hyperproliferative disease is noncancerous.

16. The method of claim 15 wherein said disorder is a benign hyperplasia of the skin or prostate.

42

17. A process for preparing a compound of the formula

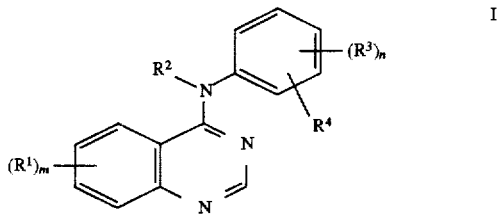

or a pharmaceutically acceptable salt or prodrug thereof, wherein:

m is 1, 2, or 3;

each $R^1$ is independently selected from the group consisting of hydrogen, halo, hydroxy, hydroxyamino, carboxy, nitro, guanidino, ureido, cyano, trifluoromethyl, and -($C_1$-$C_4$ alkylene)-W-(phenyl) wherein W is a single bond, O, S or NH;

or each $R^1$ is independently selected from $R^9$ and ($C_1$-$C_4$) -alkyl substituted by cyano, wherein $R^9$ is selected from the group consisting of $R^5$, —$OR^6$, —$NR^6R^6$, —$C(O)R^7$, —$NHOR^5$, —$OC(O)R^6$, cyano, A and —$YR^5$; $R^5$ is $C_1$-$C_4$ alkyl; $R^6$ is independently hydrogen or $R^5$; $R^7$ is $R^5$, —$OR^6$ or —$NR^6R^6$; A is selected from piperidino, morpholino, pyrrolidino, 4-$R^6$-piperazin-1-yl, imidazol-1-yl, 4-pyridon-1-yl, -($C_1$-$C_4$ alkylene)($CO_2H$), phenoxy, phenyl, phenylsulfanyl, $C_2$-$C_4$ alkenyl, and —($C_1$-$C_4$ alkylene)$C(O)NR^6R^6$; and Y is S, SO, or $SO_2$; wherein the alkyl moieties in $R^5$, —$OR^6$ and —$NR^6R^6$ are optionally substituted by one to three substituents independently selected from halo and $R^9$, and wherein the alkyl moieties of said optional substituents are optionally substituted by halo or $R^9$, with the proviso that two heteroatoms are not attached to the same carbon atom, and with the further proviso that no more than three $R^9$ groups may comprise a single $R^1$ group;

or each $R^1$ is independently selected from —$NHSO_2R^5$, phthalimido-($C_1$-$C_4$)-alkylsulfonylamino, benzamido, benzenesulfonylamino, 3-phenylureido, 2-oxopyrrolidin-1-yl, 2,5-dioxopyrrolidin-1-yl, and $R^{10}$-($C_2$-$C_4$)-alkanoylamino wherein $R^{10}$ is selected from halo, —$OR^6$, $C_2$-$C_4$ alkanoyloxy, —$C(O)R^7$, and —$NR^6R^6$; and wherein the foregoing $R^1$ groups are optionally substituted by 1 or 2 substituents independently selected from halo, $C_1$-$C_4$ alkyl, cyano, methanesulfonyl and $C_1$-$C_4$ alkoxy;

or two $R^1$ groups are taken together with the carbons to which they are attached to form a 5–8 membered ring that includes 1 or 2 heteroatoms selected from O, S and N;

$R^2$ is hydrogen or $C_1$-$C_6$ alkyl optionally substituted by 1 to 3 substituents independently selected from halo, $C_1$-$C_4$ alkoxy, —$NR^6R^6$, and —$SO_2R^5$;

n is 1 or 2 and each $R^3$ is independently selected from hydrogen, halo, hydroxy, $C_1$-$C_6$ alkyl, —$NR^6R^6$, and $C_1$-$C_4$ alkoxy, wherein the alkyl moieties of said $R^3$ groups are optionally substituted by 1 to 3 substituents independently selected from halo, $C_1$-$C_4$ alkoxy, —$NR^6R^6$, and —$SO_2R^5$; and, $R^4$ is azido or -(ethynyl)-$R^{11}$ wherein $R^{11}$ is hydrogen or $C_1$-$C_6$ alkyl optionally substituted by hydroxy, —$OR^6$, or —$NR^6R^6$;

which comprises a) treating a compound of the formula

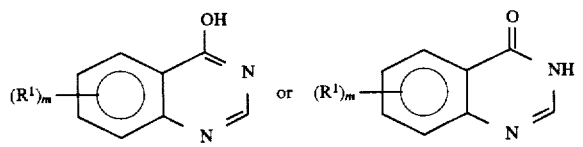

wherein $R^1$ and m are as defined above, with $CCl_4$ and $(C_6-C_{10}aryl)_3P$, optionally supported on an inert polymer, wherein the aryl moieties of said $(C_6-C_{10}aryl)_3P$ are optionally substituted by $C_1-C_6$ alkyl; and b) treating the product of step a) with a compound of the formula

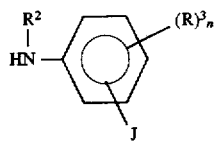

wherein $R^2$, $R^3$ and n are as defined above, and J is Y or $R^4$, wherein $R^4$ is as defined above and wherein Y is $NH_2$, Br, I or trifluoromethanesulfonyloxy, with the proviso that when J is Y then the product of step b) must further be treated with an alkyne where Y is Br, I or trifluoromethanesulfonyloxy, or an azide where Y is $NH_2$.

18. The process of claim 17 wherein each aryl group is selected from phenyl, naphth-1-yl and naphth-2-yl.

19. The process of claim 17 wherein each Ar in $(C_6-C_{10}aryl)_3P$ is phenyl.

20. The process of claim 17 wherein said $(C_6-C_{10}aryl)_3P$ is supported on an inert polymer.

21. The process of claim 20 wherein said inert polymer is a divinylbenzene-cross-linked polymer of styrene.

22. The composition of claim 3 wherein said hyperproliferative disorder is cancer.

23. The composition of claim 22 wherein said cancer is selected from the group consisting of renal, liver, kidney, colorectal, brain, lung, skin, bladder, gastric, pancreatic, breast, head, neck, oesophageal, vulval, gynecological, and thyroid cancer.

24. The composition of claim 3 wherein said hyperproliferative disorder is benign.

25. The composition of claim 24 wherein said hyperproliferative disorder is benign hyperplasia of the skin or prostate.

26. The composition of claim 25 wherein said hyperproliferative disorder is psoriasis.

27. A method of treating a hyperproliferative disorder in a mammal which comprises administering to said mammal a pharmaceutically effective amount of the compound of claim 1.

28. The method of claim 27 wherein said hyperproliferative disorder is cancer.

29. The method of claim 28 wherein said cancer is selected from the group consisting of renal, liver, kidney, colorectal, brain, lung, skin, bladder, gastric, pancreatic, breast, head, neck, oesophageal, vulval, gynecological, and thyroid cancer.

30. The method of claim 27 wherein said hyperproliferative disorder is benign.

31. The method of claim 30 wherein said hyperproliferative disorder is benign hyperplasia of the skin or prostate.

32. The method of claim 31 wherein said hyperproliferative disorder is psoriasis.

* * * * *

UNITED STATES PATENT AND TRADEMARK OFFICE
CERTIFICATE OF CORRECTION

| | |
|---|---|
| PATENT NO. | : 5,747,498 |
| APPLICATION NO. | : 08/653786 |
| DATED | : May 5, 1998 |
| INVENTOR(S) | : Rodney Caughren Schnur et al. |

It is certified that error appears in the above-identified patent and that said Letters Patent is hereby corrected as shown below:

Column 38,
Line 26, delete "X is halo or hydroxy;".

Column 39,
Line 9, delete "–SO$_2$R ;" and insert -- –SO$_2$R$^5$; --.

Signed and Sealed this

Sixteenth Day of September, 2008

JON W. DUDAS
*Director of the United States Patent and Trademark Office*